United States Patent
Lofstrom et al.

(10) Patent No.: US 8,754,390 B2
(45) Date of Patent: Jun. 17, 2014

(54) GENERATING PULSE PARAMETERS IN A PARTICLE ANALYZER

(75) Inventors: Christopher D. Lofstrom, Fort Collins, CO (US); Daniel N. Fox, Fort Collins, CO (US); Thomas L. Thrasher, Fort Collins, CO (US); David C. Neckels, Berthoud, CO (US)

(73) Assignee: Beckman Coulter, Inc., Brea, CA (US)

( * ) Notice: Subject to any disclaimer, the term of this patent is extended or adjusted under 35 U.S.C. 154(b) by 554 days.

(21) Appl. No.: 13/044,685

(22) Filed: Mar. 10, 2011

(65) Prior Publication Data

US 2011/0303859 A1 Dec. 15, 2011

Related U.S. Application Data

(60) Provisional application No. 61/312,616, filed on Mar. 10, 2010.

(51) Int. Cl.
  *G01N 21/64* (2006.01)
  *G01N 21/84* (2006.01)
  *G01J 3/30* (2006.01)
  *G01P 3/36* (2006.01)

(52) U.S. Cl.
  USPC ............ 250/573; 250/458.1; 250/459.1; 356/28; 702/19; 702/22; 702/32; 702/189

(58) Field of Classification Search
  USPC ............ 250/573, 574, 576, 459.1, 458.1; 356/28; 702/189, 128, 127, 21, 22, 29, 702/31, 32
  See application file for complete search history.

(56) References Cited

U.S. PATENT DOCUMENTS

| | | | |
|---|---|---|---|
| 3,936,741 A * | 2/1976 | Coulter et al. | 377/50 |
| 4,325,483 A | 4/1982 | Lombardo et al. | |
| 4,953,978 A * | 9/1990 | Bott et al. | 356/336 |
| 5,056,918 A * | 10/1991 | Bott et al. | 356/336 |
| 5,104,221 A * | 4/1992 | Bott et al. | 356/336 |
| 5,272,354 A * | 12/1993 | Kosaka | 250/574 |
| 6,970,799 B2 * | 11/2005 | Kleefstra | 702/128 |
| 7,590,500 B2 * | 9/2009 | Jochum et al. | 702/85 |
| 7,945,428 B2 * | 5/2011 | Fox et al. | 702/189 |
| 8,004,674 B2 * | 8/2011 | Ball et al. | 356/317 |
| 8,290,751 B2 * | 10/2012 | Fox et al. | 702/189 |
| 8,528,427 B2 * | 9/2013 | Vrane et al. | 73/865.5 |
| 2004/0068389 A1 * | 4/2004 | Kleefstra | 702/155 |
| 2007/0124089 A1 * | 5/2007 | Jochum et al. | 702/32 |
| 2007/0269348 A1 * | 11/2007 | van den Engh et al. | 422/100 |
| 2008/0319680 A1 * | 12/2008 | Fox et al. | 702/21 |
| 2009/0171590 A1 * | 7/2009 | Puskas et al. | 702/19 |
| 2010/0172020 A1 * | 7/2010 | Price et al. | 359/381 |

(Continued)

*Primary Examiner* — John Lee
(74) *Attorney, Agent, or Firm* — K&L Gates LLP; Louis C. Cullman; Georgia Kefallinos

(57) ABSTRACT

A method is provided for generating measurement parameters for a particle sample in a particle analyzer. The method includes, interrogating the particle sample with a triggering interrogator and one or more secondary interrogators respectively positioned along a length of an interrogation area, generating respective pulses based upon the interrogation of a first particle from the particle sample, determining a primary pulse detection window based upon a triggering pulse, determining a search interval to find a secondary pulse based upon factors including the primary pulse detection window and a laser delay, adjusting the search interval for laser delay variation dynamically based on the interrogation of the first particle, identifying the secondary pulse in the adjusted search interval, and processing the secondary pulse to determine a peak value of the secondary pulse. Corresponding apparatus are also provided.

25 Claims, 23 Drawing Sheets

(56) References Cited

U.S. PATENT DOCUMENTS

| | | | |
|---|---|---|---|
| 2010/0193703 A1* | 8/2010 | Kimura et al. | 250/459.1 |
| 2010/0256943 A1* | 10/2010 | Donnenberg et al. | 702/104 |
| 2010/0302536 A1* | 12/2010 | Ball et al. | 356/317 |
| 2011/0010144 A1* | 1/2011 | Fox et al. | 703/2 |
| 2011/0030808 A1* | 2/2011 | Chiou et al. | 137/13 |
| 2011/0164246 A1* | 7/2011 | Riddell | 356/301 |
| 2011/0213591 A1* | 9/2011 | Fox et al. | 702/189 |
| 2011/0221892 A1* | 9/2011 | Neckels et al. | 348/135 |
| 2011/0303859 A1* | 12/2011 | Lofstrom et al. | 250/573 |
| 2011/0309266 A1* | 12/2011 | Hayashi | 250/459.1 |
| 2012/0075389 A1* | 3/2012 | Clarke et al. | 347/73 |
| 2012/0329665 A1* | 12/2012 | Rimm et al. | 506/9 |
| 2013/0013226 A1* | 1/2013 | Fox et al. | 702/46 |
| 2013/0200277 A1* | 8/2013 | Li et al. | 250/459.1 |

\* cited by examiner

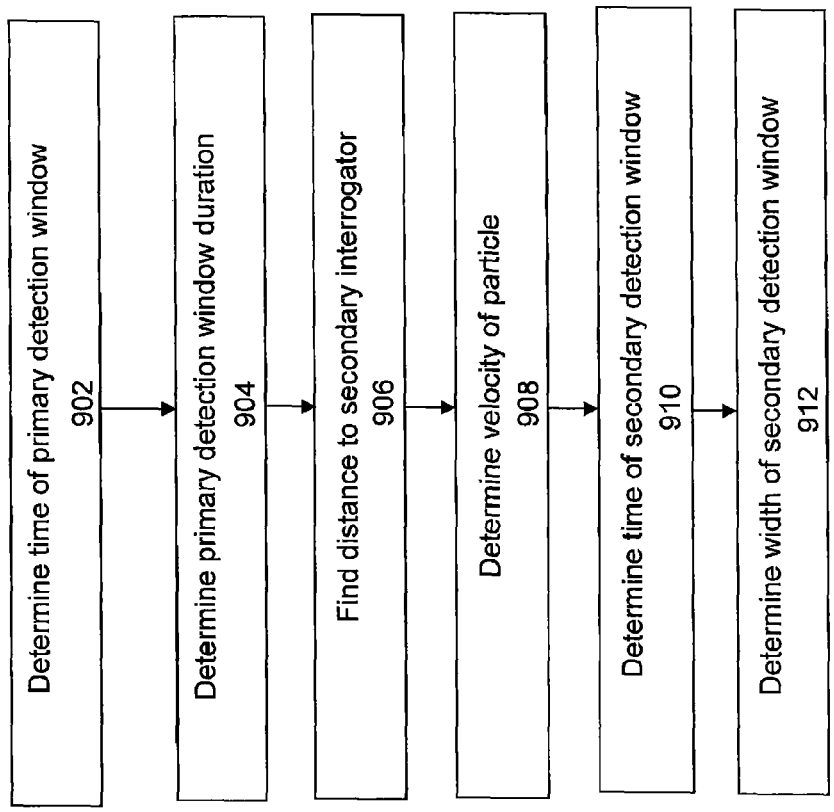

GENERATING PULSE PARAMETERS IN A PARTICLE ANALYZER

PRIORITY CLAIM

This patent application claims priority pursuant to 35 U.S.C. §119(e) to U.S. Provisional Patent Application 61/312,616, filed on Mar. 10, 2010, which is hereby incorporated by reference in its entirety.

BACKGROUND

1. Field of the Invention

This invention relates to the analysis of particle samples using a particle analyzer.

2. Background

Particle analyzers enable the rapid analysis of particle samples to detect various characteristics of the sample as well as to detect characteristics of the individual particles. Some particle analyzers also include functionality to sort the particles according to one or more detected characteristics.

Particle analyzers, such as flow cytometers and hematology analyzers, are frequently used to analyze biological cell samples such as blood or tissue. In a flow cytometer, a cell sample is subjected to interrogation in an interrogation area along the flow path of the sample. Typically, cells in a sheath fluid pass through a flow cell, one by one, where they are interrogated by probes, including one or more beams of light. For example, one or more laser light sources can be positioned in the flow cell along the path of flow of the cell stream. In other flow cytometers, such as in jet-in-air flow cytometers, cells in a sheath fluid are interrogated by one or more probes outside of a flow cell. Several measurements are generated for each passing cell. As a cell passes through the interrogation area, resulting light characteristics, such as light scatter, light loss, and fluorescence, are measured by detectors. The measured light characteristics are used to generate corresponding electrical pulses for each interrogated cell. The electrical pulses are analyzed to determine parameters of the cell, such as, pulse peak, pulse width, and pulse area. A sorting flow cytometer, for example, can sort cells of different types into receptacles.

Prior to being interrogated, the cell sample can be prepared using various fluorochromes and/or reagents to mark specific cell types. Each fluorochrome and/or reagent can bind to cells of different types. As the cells pass through the interrogation area, laser light sources excite the fluorochromes and/or reagents. By increasing the number of different fluorochromes and/or reagents that can be detected, a cell sample can be analyzed for the presence of an increasing range of cell types. However, each laser light source, for example, can only excite fluorochromes within a limited wavelength range. It is thus desirable to use multiple laser light sources to enable the detection of a broader range of wavelengths and frequencies.

But, multiple laser light sources that are positioned along the flow path of the cell stream can lead to increased coincidence and spillover if the distances between the light sources are too small. Coincidence, i.e., the detection of more than one particle within a detection window, leads to aborting of affected particles from the analyzed sample. Spillover, i.e., the detection of the optical response generated by adjacent light sources, cause inefficiencies due to the need to compensate for spillover effects. Therefore, to avoid increased coincidence and spillover, the laser light sources are positioned with substantial distance between each other. By increasing the distance between the multiple laser light sources, the efficiency of the particle analyzer can be improved by reducing coincidences and spillover. Increased distance between light sources also enables the analysis of a range of particle sizes, thus increasing the utility of the particle analyzer even more. However, increasing the distance between laser light sources led to unexpectedly finding that the parameters generated for particles are often not accurate when the distances between laser light sources are increased.

Therefore, it is desired to improve the accuracy of parameters generated in particle analyzers that utilize multiple light sources.

BRIEF SUMMARY

The present invention is directed towards the analysis of particle analyzer data. In one embodiment, a method of generating measurement parameters for a particle sample in a particle analyzer, includes: interrogating the particle sample with interrogators respectively positioned along a length of an interrogation area, the interrogators comprising a triggering interrogator and one or more secondary interrogators; generating respective pulses based upon the interrogation of a first cell from the particle sample, wherein the pulses comprise a triggering pulse corresponding to the triggering interrogator and a secondary pulse corresponding to one of the secondary interrogators; determining a primary pulse detection window based upon the triggering pulse; determining a search interval to find the secondary pulse based upon factors including the primary pulse detection window and a laser delay; adjusting the search interval for laser delay variation dynamically based on the interrogation of first particle; identifying the secondary pulse in the adjusted search interval; and processing the secondary pulse to determine a peak value of the secondary pulse.

In another embodiment, a method of generating measurement parameters for a particle sample in a particle analyzer, includes: interrogating the particle sample with interrogators respectively positioned along a length of an interrogation area, the interrogators comprising a triggering interrogator and one or more secondary interrogators; generating respective pulses based upon the interrogation of a first cell from the particle sample, wherein the pulses comprise a triggering pulse corresponding to the triggering interrogator and a secondary pulse corresponding to one of the secondary interrogators; determining a primary pulse detection window based upon the triggering pulse; determining a secondary pulse detection window based upon factors including the primary pulse detection window and a laser delay; detecting characteristics of a perturbation signal applied to the first particle; shifting the secondary pulse detection window based upon the characteristics of the perturbation signal. identifying the secondary pulse in the adjusted search interval; and processing the secondary pulse to determine measurement parameters of the secondary pulse.

Yet another embodiment is a particle analyzer including at least one processor, a particle interrogator, and a pulse analyzer. The particle interrogator is configured to: interrogate a particle sample with interrogators respectively positioned along a length of an interrogation area, the interrogators comprising a triggering interrogator and one or more secondary interrogators; and generate respective pulses based upon the interrogation of a first cell from the particle sample, wherein the pulses comprise a triggering pulse corresponding to the triggering interrogator and a secondary pulse corresponding to one of the secondary interrogators. The pulse analyzer includes a primary pulse detection window creator configured to determine a primary pulse detection window based upon the triggering pulse, a secondary pulse detection window creator configured to determine, based upon factors including the primary pulse detection window and a laser delay, a search interval corresponding to one of said secondary interrogators, and a secondary pulse parameter generator. The secondary pulse detection window creator can also be configured to adjust the search interval for laser delay variation dynamically based on the interrogation of the first particle. The secondary pulse parameter generator is configured to identify a secondary pulse in the adjusted search interval, and process the secondary pulse to determine a peak value of the secondary pulse.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

FIG. 9 is an illustration of a method to determine a secondary pulse detection window, according to an embodiment of the present invention.

Figure 1:
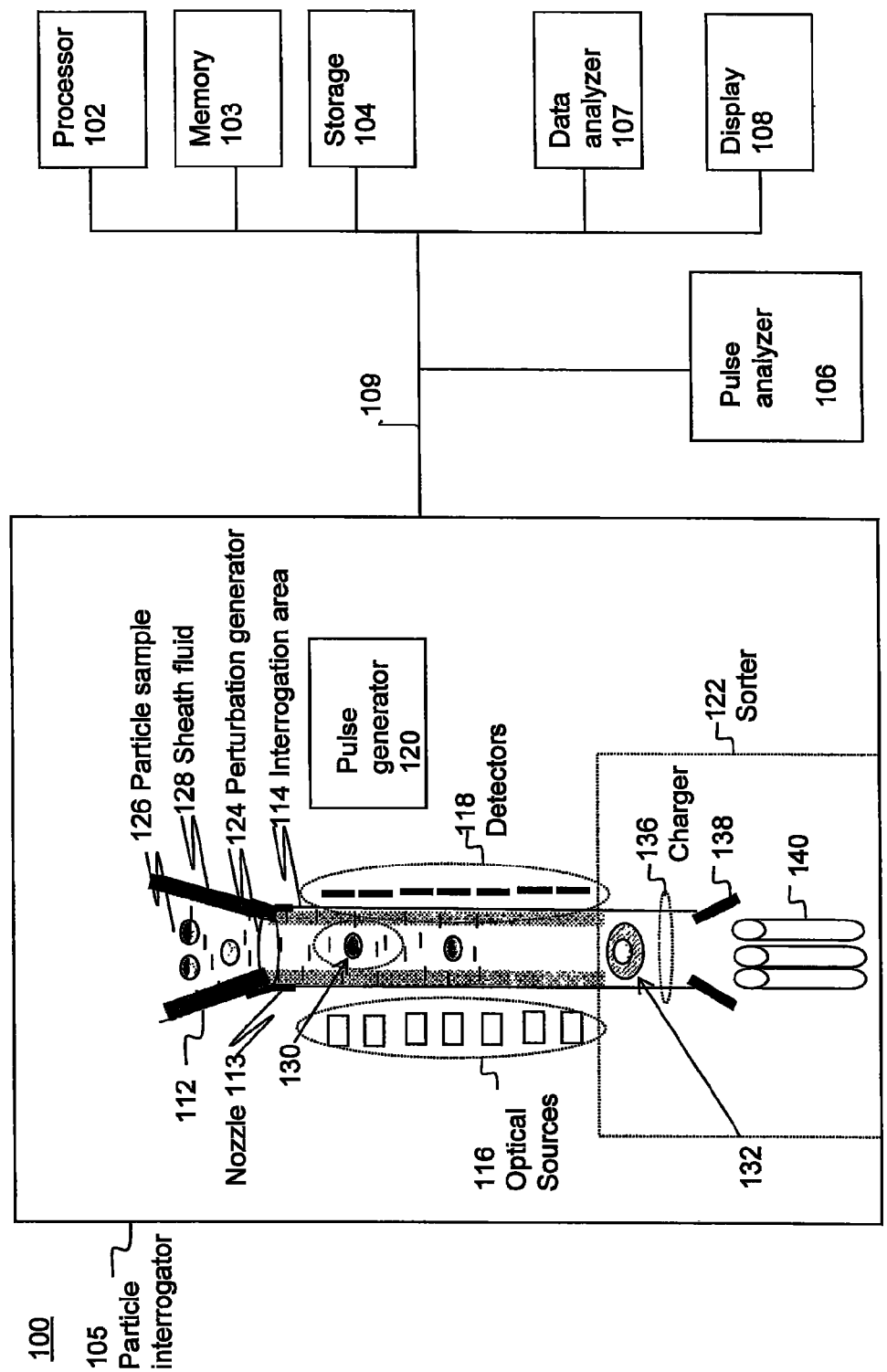
FIG. 1 is an exemplary particle analyzer, according to an embodiment of the present invention.

The features and advantages of the present invention will become more apparent from the detailed description set forth below when taken in conjunction with the drawings. In the drawings, like reference numbers generally indicate identical, functionally similar, and/or structurally similar elements. Generally, the drawing in which an element first appears is indicated by the leftmost digit(s) in the corresponding reference number.

DETAILED DESCRIPTION

The present invention relates to particle analysis. While the present invention is described herein with reference to illustrative embodiments for particular applications, it should be understood that the invention is not limited thereto. Those skilled in the art with access to the teachings herein will recognize additional modifications, applications, and embodiments within the scope thereof and additional fields in which the invention would be of significant utility.

As described in the background section above, it is desired that multiple optical interrogators, such as laser sources and detectors, are available to interrogate a cell sample. Multiple laser interrogators, each capable of exciting and detecting light from a part of the frequency spectrum, positioned along the length of an interrogation area in the flow path of the sample can subject the cell sample to interrogation over a wide range of wavelengths and frequencies, thus increasing the utility and effectiveness of a single run of the cell sample through the particle analyzer. Other factors, such as, the decreasing cost of lasers, availability of an increasing variety of fluorochromes, and the availability of increased processing power, facilitate the development of particle analyzers with a larger number of optical interrogators than available on conventional devices. However, the inventors discovered that increasing the number of optical interrogators, and more particularly, increasing the distance between optical interrogators, can introduce unintended consequences and inconsistencies in the generation of parameters that describe the properties of particles. In some particle analyzers, such as sorting flow cytometers, where the cell stream flowing through the interrogation area is perturbed (e.g., to facilitate forming of drops to enable sorting) the errors involved in generating parameters according to conventional methods in devices with a larger number of optical interrogators can be substantial. Embodiments of the present invention enable the generation of accurate parameters, such as pulse peak, pulse width, and pulse area, in particle analyzers having multiple optical interrogators. By enabling the use of multiple optical interrogators, embodiments of the present invention increase the ability of a particle analyzer to detect a variety of particle characteristics in a single run. By enabling multiple optical interrogators to be placed at substantial distances from each other while still generating accurate parameters, embodiments of the present invention increase the efficiency of particle analyzers by reducing or eliminating coincidence and spillover. In addition, by permitting multiple optical interrogators to be placed at substantial distances from each other, embodiments of the present invention enable the analysis of particles of various sizes, for example, by using different nozzle configurations.

Particle Analyzer

FIG. 1 is an illustration of a particle analyzer 100, according to an embodiment of the present invention. Particle analyzer 100 can, for example, be a sorting flow cytometer. Particle analyzer 100 comprises one or more processors 102, a memory 103, a storage 104, a particle interrogator 105, and a pulse analyzer 106. In some embodiments, particle analyzer 100 can also include a data analyzer 107 and a display 108.

One or more processors 102 can include one or more of, a central processing unit (CPU), a field programmable gate array (FPGA), an application specific integrated circuit (ASIC), digital signal processor (DSP), or like instruction processing device. Memory 103 generally includes a volatile memory such as random access memory for temporary storage of data and processing instructions. Storage 104 generally includes non-volatile storage for storing processing instructions, configuration data, particle data, and results of processing. Storage 104 can include computer readable storage mediums such as hard disk, flash storage, optical disk, floppy disk, and the like. Particle interrogator 105 enables a particle sample to be subjected to interrogation by multiple light sources in an interrogation area. Pulse analyzer 106 includes the functionality to generate parameters corresponding to individual particles in the particle sample. For example, pulse analyzer 106 accepts as input electrical pulses generated by the particle interrogator 105 for respective particles, and generates parameters such as a pulse peak, pulse width, and pulse area. Pulse analyzer 106 is further described below with respect to FIG. 5. The parameters generated in pulse analyzer 106 are then processed by data analyzer 107 and reported and/or displayed using display 108. Communications infrastructure 109 interconnects the various components of particle analyzer 100, and can include connection devices, such as, peripheral component interconnect (PCI) bus, universal serial bus (USB), Firewire, Ethernet, or like devices.

Data analyzer 107 receives parameters generated by pulse analyzer 106 and further reports and/or processes the data by classifying, counting, and analyzing the data. Data analyzer 107 can include functionality to filter the received data for erroneous data. Some embodiments of the present invention improve the quality of the parameters that are submitted to data analyzers such as data analyzer 107. Data analyzer 107 and/or display 108 can be external to the particle analyzer 100 in some embodiments. Data analyzer 107, for example, can be configured on a separate computer coupled to the particle analyzer 100 through a network (not shown). In an embodiment data analyzer 107 can include analysis software such as SUMMIT™ flow cytometric data analysis software from Beckman Coulter.

Particle interrogator 105 includes a particle sample dispensing area 112, a sample injecting nozzle 113, an interrogation area 114, a plurality of light sources 116, a plurality of light detectors 118, and an electrical pulse generator 120. Particle sample dispensing area 112 provides for holding a particle sample 126 and a sheath fluid 128. A particle sample can, for example, be a whole blood sample or a whole blood sample prepared by adding one or more fluorochromes and/or reagents.

Nozzle 113 enables the injecting of the particle sample, including the sheath fluid, to be injected into the interrogation area 114. Nozzle 113 is, in general, configured to inject a hydro-dynamically focused particle sample such that particles, such as particle 130, flow through interrogation area 114 in single file, one particle after another. In some embodiments, nozzle 113 can be configured with the size of nozzle (i.e., diameter of nozzle) and the sheath fluid pressure.

Over the length of interrogation area 114, a plurality of light sources 116 and a plurality of corresponding light detectors 118 are positioned. Interrogation area 114, in some embodiments, can comprise a flow cell. In some embodiments, such as in jet-in-air flow cytometers, interrogation area can comprise an area, not within a flow cell, in the flow path of the particle sample. A pairing of light source and corresponding detector can be referred to as an interrogator. In the illustrated embodiment, seven light sources 116 and seven corresponding light detectors 118 are shown positioned along the length of the interrogation area. In an embodiment, light sources 116 can comprise laser light sources having different wavelengths. In the interrogation area, respective ones of the light sources 116 illuminate each particle as it passes through a detection area corresponding to the respective light source, and the resulting optical signals including light scatter and/or fluorescence are detected by the corresponding detectors 118. Each detector can comprise a pinhole (not separately shown) and an optical detector to detect light scatter and/or fluorescence. The optical signals from each detector are converted to respective electrical signals, such as voltage signals, by the electrical pulse generator 120. The resulting electrical signal corresponding to the optical response generated by the interrogation of a single cell by an interrogator is referred to as a pulse. The pulses are processed by pulse analyzer 106 to identify various parameters corresponding to particles and to provide the parameters to data analyzer 107. Pulse analyzer 106, based on identified parameters, can also control the operation of the particle interrogator 106 through, for example, a control module (not shown) to perform such tasks as configuring the nozzle, configuring the light sources and detectors, and configuring the optional particle sorter 122.

In some embodiments, a particle sorter 122 is used to sort particles according to various characteristics. Associated with particle sorter 122 are a particle charging device 136 and a perturbation generator 124. Perturbation generator 124 can be associated with nozzle 113 to generate a perturbation of the particle stream injected into the interrogation area. In an embodiment, perturbation generator 124 is located in a nozzle assembly, such as nozzle 113, above the nozzle exit. For example, a pressure wave corresponding to a sine wave can be generated by the perturbation generator. The pressure wave is configured so that the particle stream can deterministically form droplets, ideally with each droplet containing a single particle, in a droplet forming area 132. In an embodiment, perturbation generator 124 comprises a piezoelectric crystal oscillator with a configurable oscillating frequency. In an embodiment, the frequency, amplitude, and phase of the perturbation wave are configurable. The droplet forming area 132 occurs after the optical interrogators in the path of the particle stream in the interrogation area. An electrical charge can be applied to each droplet by a charging device 136. In an embodiment, charging device 136 is located in the droplet forming area 132. In another embodiment, charging device may be located before the interrogation area. For example, a charging device located above the interrogation area can convey a charge to a droplet in droplet forming area 132 through the sheath fluid. The droplet can be charged according to the characteristics of the particle contained in the droplet. When a droplet enters the sorter, charged plates 138 direct the droplet to one of the receptacles 140. Particle sorter 122 is configured to have each of the receptacles 140 collect particles with like characteristics.

The interrogation of a particle sample includes injection of the sample, with or without perturbation, into the interrogation area and the interrogation of particles by probes along the interrogation area. As noted previously, each interrogator causes a pulse representing same or different aspects of the same particle to be generated. Pulse analyzer 106 receives a signal stream containing the generated pulses from the particle interrogator 105, and is configured to identify pulses corresponding to each respective particle and interrogator.

The spatial interval between respective light sources 116 can be determined based on various criteria, such as, the number of light sources, length of the interrogation area, size of particles, the amplitude of the pressure wave that can be generated to encourage drop-forming, power of the light sources, cell event rate, level of tolerable error, and the like.

Positioning light sources close to each other can increase spectral overlap by allowing signals corresponding to adjacent spectral frequencies to spillover to the detection ranges of each other. Spectral overlap is undesirable because additional compensation is required to obtain valid signals for analysis. However, when light sources are spaced further apart, variations can occur as to the time when a particle actually passes through the detection area of a detector and the time at which it was expected in the detection area. When perturbation of the particle stream is introduced, such as by using perturbation generator 124, the variation in velocity among particles is increased which in turn can lead to increased errors in detecting pulses. Conventional particle analyzers did not, to the knowledge of the inventors, recognize the relationship between the inter-interrogator spacing, arrival time of pulses at secondary interrogators, and the perturbation signal applied to the cell stream. Embodiments of the present invention incorporate features in particle analyzers to overcome inaccuracies in generated parameters when such a relationship exists.

Figure 2:
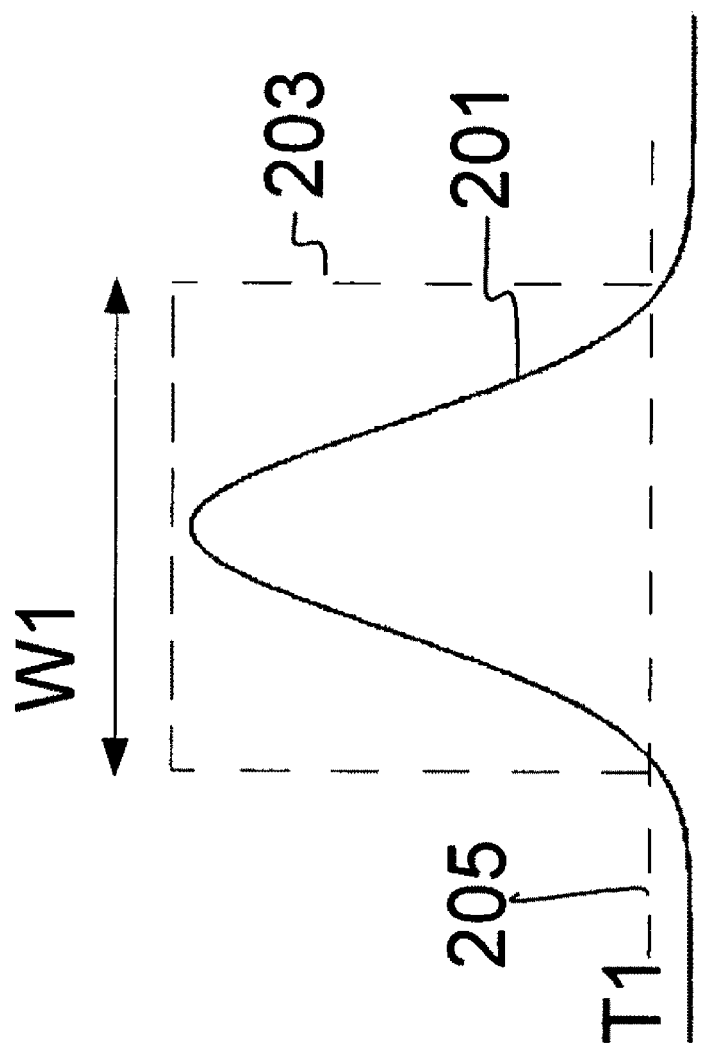
FIG. 2 is an illustration of an exemplary pulse and its corresponding detection window.
Figure 3A:
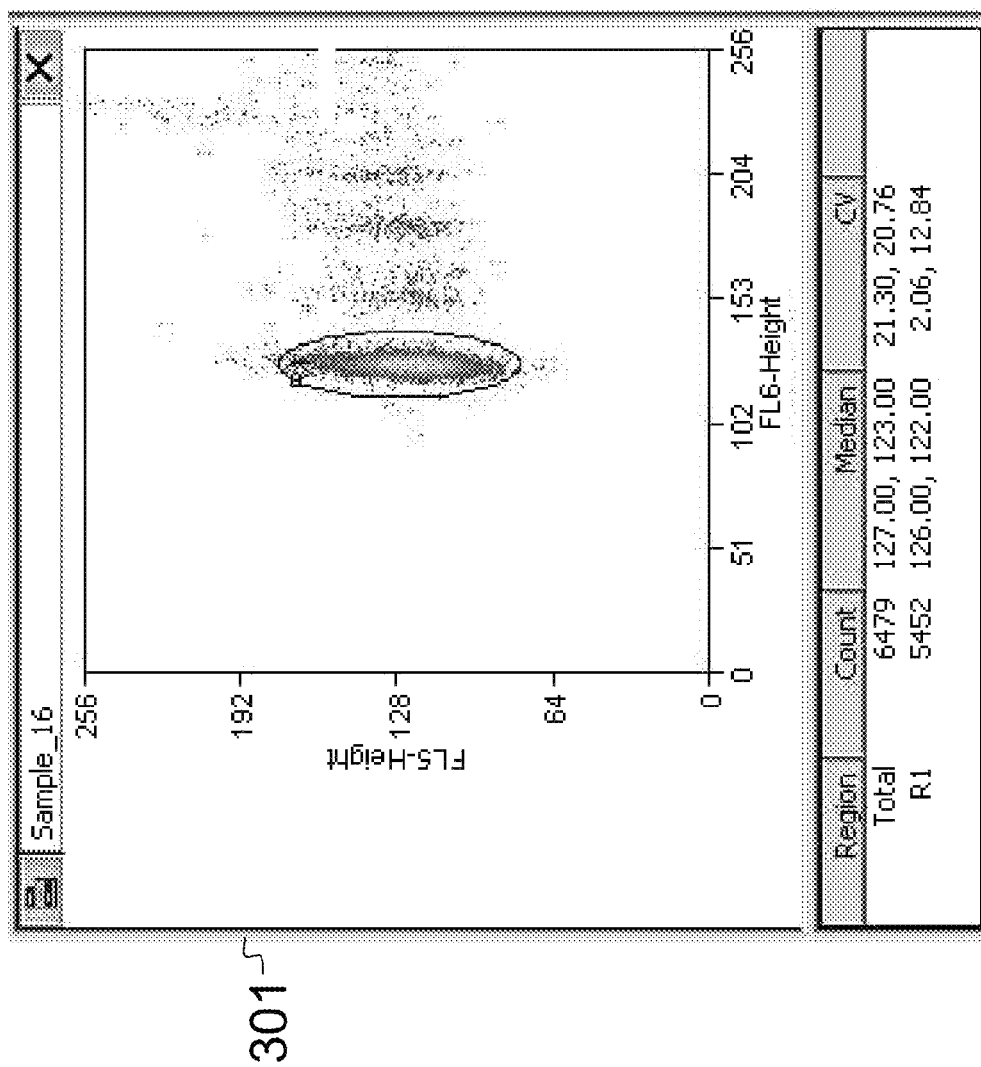
FIG. 3 is an illustration of the effects of introducing a perturbation signal in a particle analyzer.
Figure 3B:
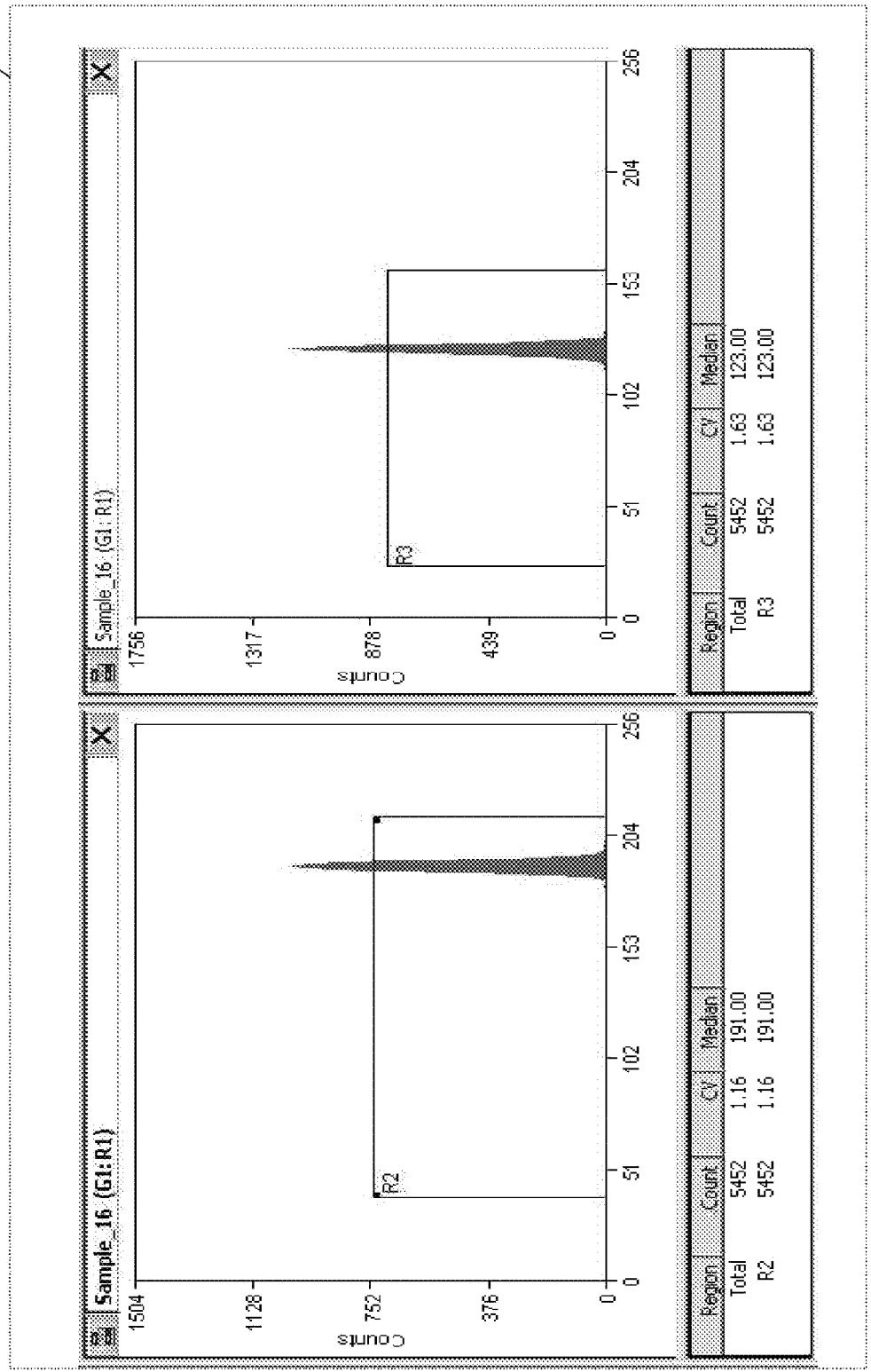
Figure 3C:
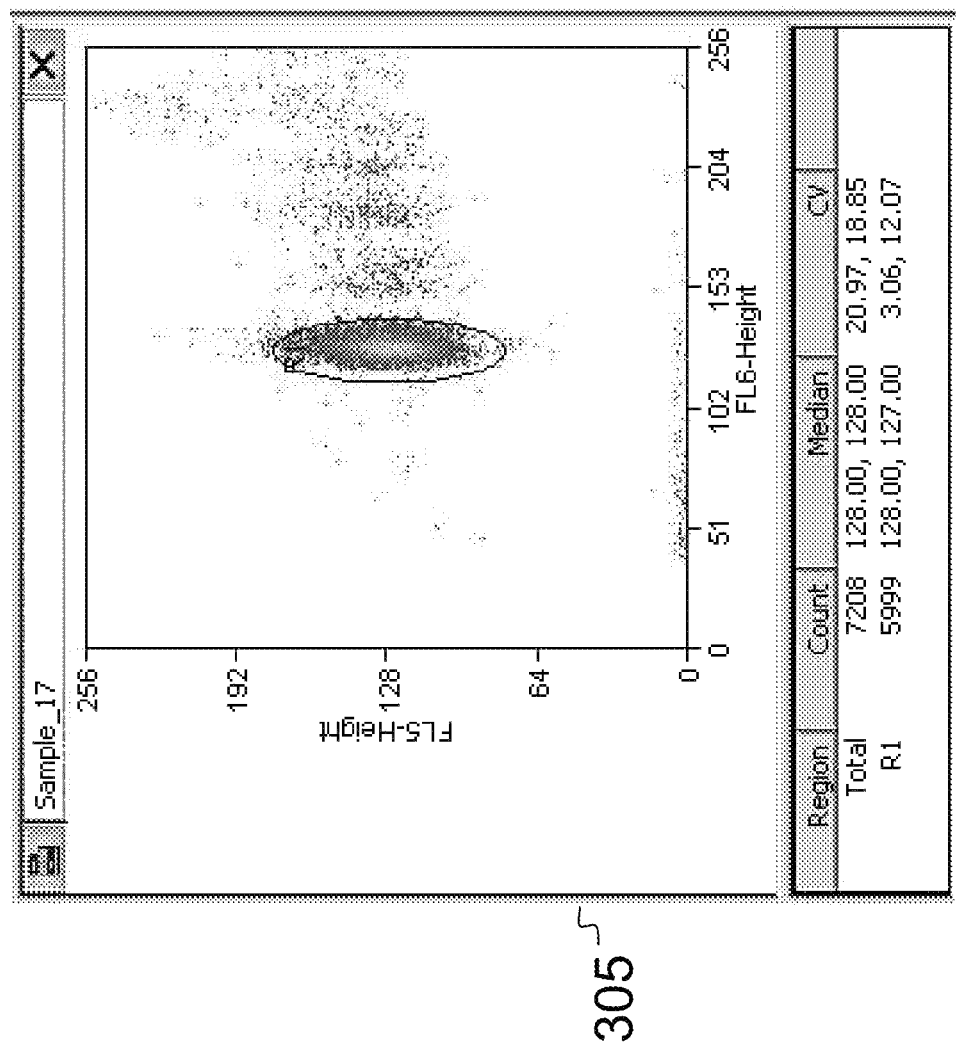
Figure 3D:
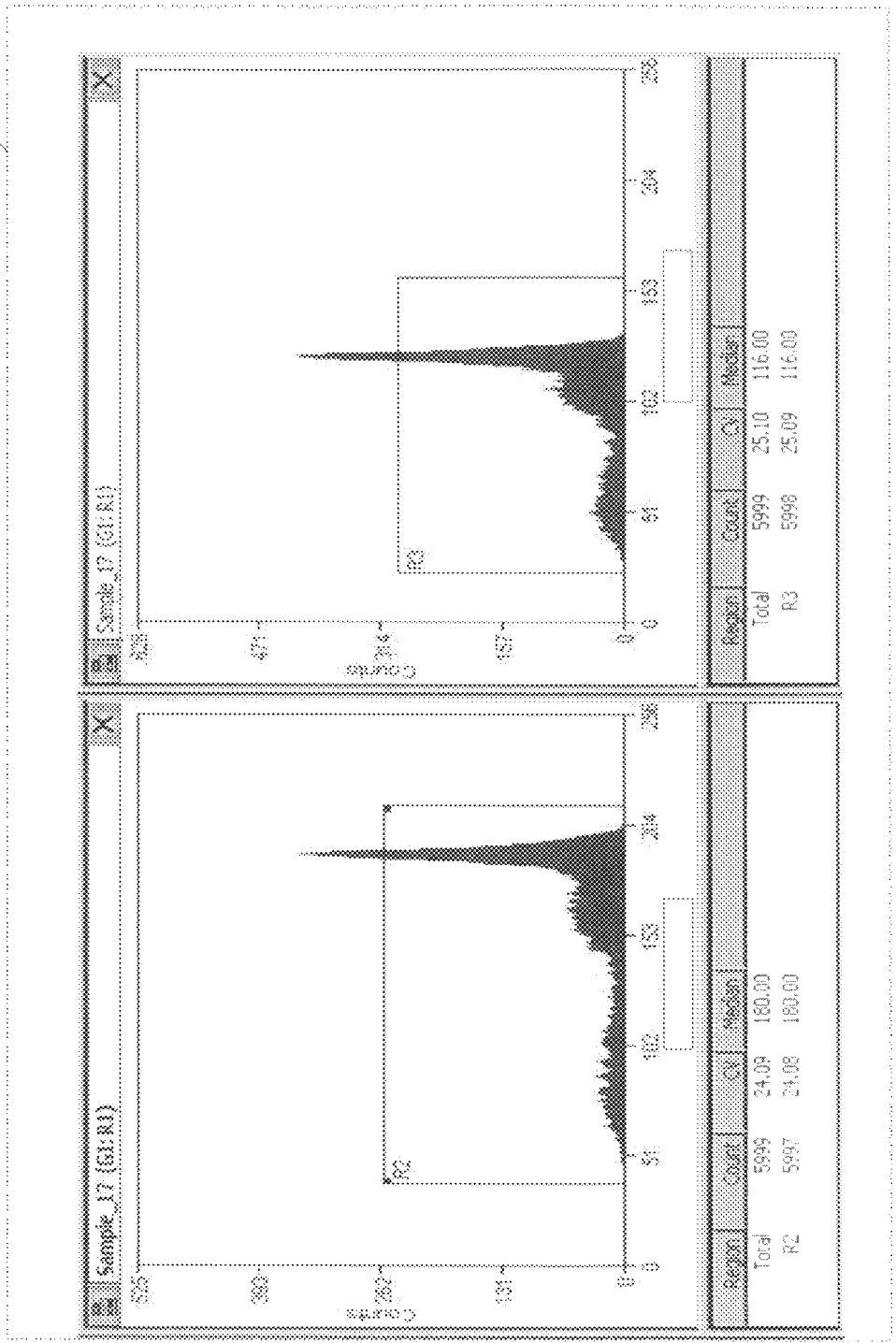

FIG. 2 is an illustration of a pulse, a pulse detection window, and pulse detection threshold. Pulse analyzer 106 detects pulses in the incoming signal stream from the particle interrogator by creating a pulse detection window corresponding to a particular interrogator and then finding a pulse relative to that detection window. Pulse 201, for example, is seen within pulse detection window 203. Pulse 201 is detected as a pulse when the corresponding signal remains at or above a pulse detection threshold 205. The pulse detection threshold 205 can be preconfigured. In the triggering interrogator, the detection window width is determined based on the duration of the pulse above the threshold. The triggering interrogator can be user selectable. For example, the interrogator closest to the input to the interrogation area can be selected as the triggering interrogator. The triggering interrogator can be selected based on the type of cell sample and/or type of analysis that is desired. The pulse and the pulse detection window corresponding to the trigger interrogator can be referred to as, respectively, primary pulse and primary pulse detection window. Non-trigger interrogators, corresponding pulses, and corresponding detection windows, are referred to as, respectively, secondary interrogator, secondary pulse, and secondary pulse detection window. Laser delay (LD) is the distance in time between the primary pulse detection window and a secondary pulse detection window. The laser delay can be dependent on the spatial distance between the respective interrogators and the velocity of respective particles.

Laser Delay Variation

FIG. 3 is an illustration of the differences that can be caused by introducing a perturbation to the particle stream when multiple optical interrogators are positioned along an interrogation area so that substantial laser delays exist between interrogators. As described above, the perturbation may be a pressure wave introduced to the particle stream. The perturbation can be introduced using a perturbation generator 124 positioned within or in proximity to nozzle 113. Graph 301 illustrates FITC (a type of fluorescence) and side scatter measurements based on the pulse corresponding to the trigger interrogator when there is no perturbation. Graph 305 illustrates the same measurements for the same sample based on the pulse corresponding to the first interrogator when a perturbation has been introduced. Graphs 301 and 305 illustrate that the pulses corresponding to the trigger interrogator are not substantially affected by the perturbation, i.e., despite the perturbation the pulse corresponding to the first interrogator can be accurately determined. In this example, the trigger interrogator is configured as the first, i.e., closest to the nozzle, of seven interrogators.

However, graphs 302 and 306 represent, fluorescence measurements based on the pulses corresponding to the last interrogator that is located furthest from the first interrogator. Graph 302, as shown by the narrow variation in fluorescence measurements, illustrates that when there is no perturbation, the pulses can be measured without substantial error even at the seventh interrogator. Graph 306, however, as shown by the wide variation in fluorescence measurements, illustrates that when perturbation exists in the particle stream, the measurements corresponding to the distant interrogators can have a substantial variance.

Figure 4:
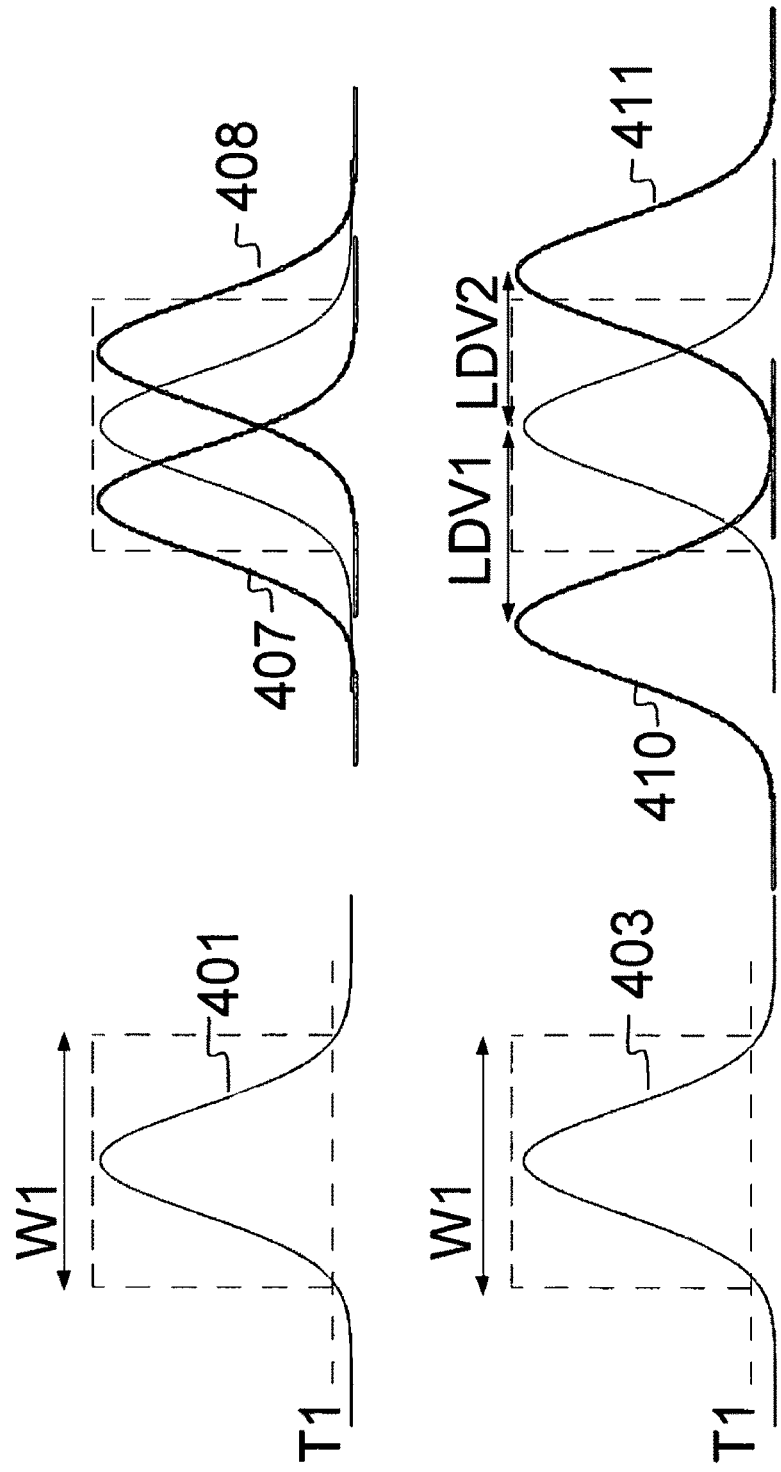
FIG. 4 is an illustration of characteristics of a pulse with respect to characteristics of a perturbation signal applied to the cell stream.

FIG. 4 is an exemplary illustration of pulses relative to corresponding pulse detection windows. Pulses 401 and 403, respectively show that the pulse detected for the trigger interrogator (i.e., primary interrogator) is positioned accurately within the corresponding pulse detection window, in the cases of some perturbation (e.g., a perturbation signal amplitude of 15V), and a relatively high level of perturbation (e.g., a perturbation signal amplitude of 40V). When perturbation signal amplitude is at 15V, pulses 407 and 408, that respectively represent the corresponding pulses at an interrogator preceding the trigger interrogator in the interrogation area and an interrogator positioned after the trigger interrogator, illustrate that they can have substantial portions of the pulse either before or after the corresponding pulse detection window. Pulses 410 and 411 illustrate that, when perturbation signal amplitude is increased, the difference in arrival of the pulse with respect to the corresponding pulse detection window increases. For example, the expected arrival time can be measured relative to the center of the pulse detection window. The difference in arrival times of the pulse compared to the expected arrival time based on the corresponding pulse detection window is referred to as laser delay variation (LDV). Thus, the laser delay variation increases with the increase in the perturbation amplitude.

Pulse Analyzer

Figure 5:
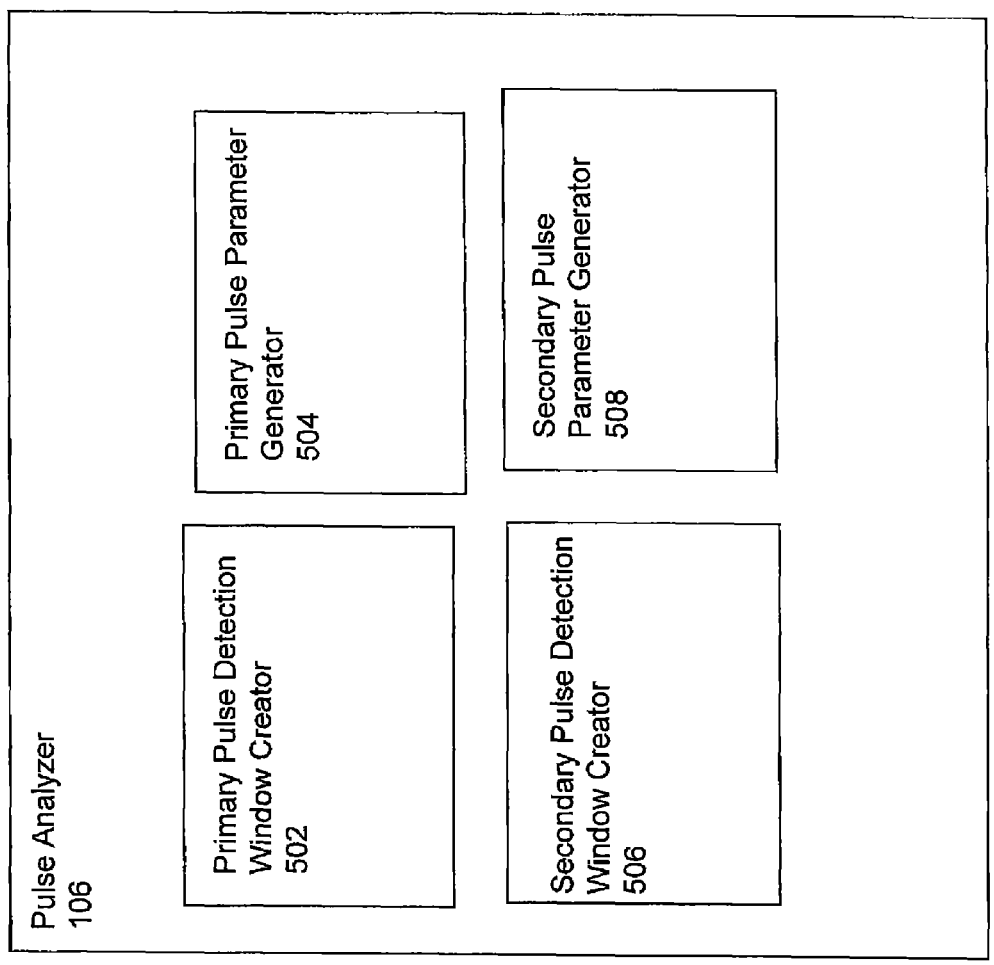
FIG. 5 is an illustration of a pulse analyzer, according to an embodiment of the present invention.

FIG. 5 is an illustration of a pulse analyzer 106. According to an embodiment, pulse analyzer 106 comprises a primary pulse detection window creator 502, a primary pulse parameter generator 504, a secondary pulse detection window creator 506, and a secondary pulse parameter generator 508. It is understood that other components, such as a control module (not shown) to control the particle interrogator 105 based on generated parameters can be included in pulse analyzer 106. Pulse analyzer 106 can be implemented in software, firmware, hardware, or any combination thereof. In an embodiment, pulse analyzer 106 is implemented in FPGA firmware.

Primary pulse detection window creator 502, in an embodiment, is configured to determine the primary pulse detection window for each particle detected in the interrogation area. The determining of the primary pulse detection window is described below with respect to FIG. 6.

Primary pulse parameter generator 504, in an embodiment, is configured to determine parameters such as pulse peak, pulse width, and pulse area, for each particle, based on the primary pulse. The determination of primary pulse parameters is described below with respect to FIG. 6.

Secondary pulse detection window creator 506, in an embodiment, is configured to determine a search interval corresponding to one or more secondary interrogators for respective particles detected in the interrogation area. Secondary pulse detection window creator 506 also includes the functionality to adjust the search interval based on laser delay variation. The determination and adjustment of the search interval for secondary pulses is described below with respect to FIG. 6.

Secondary pulse parameter generator 508, in an embodiment, is configured to determine parameters such as pulse peak, pulse width, and pulse area, for each particle, based on the primary pulse. Determination of secondary pulse parameters is described below with respect to FIG. 6.

Method to Generate Parameters

Figure 6:
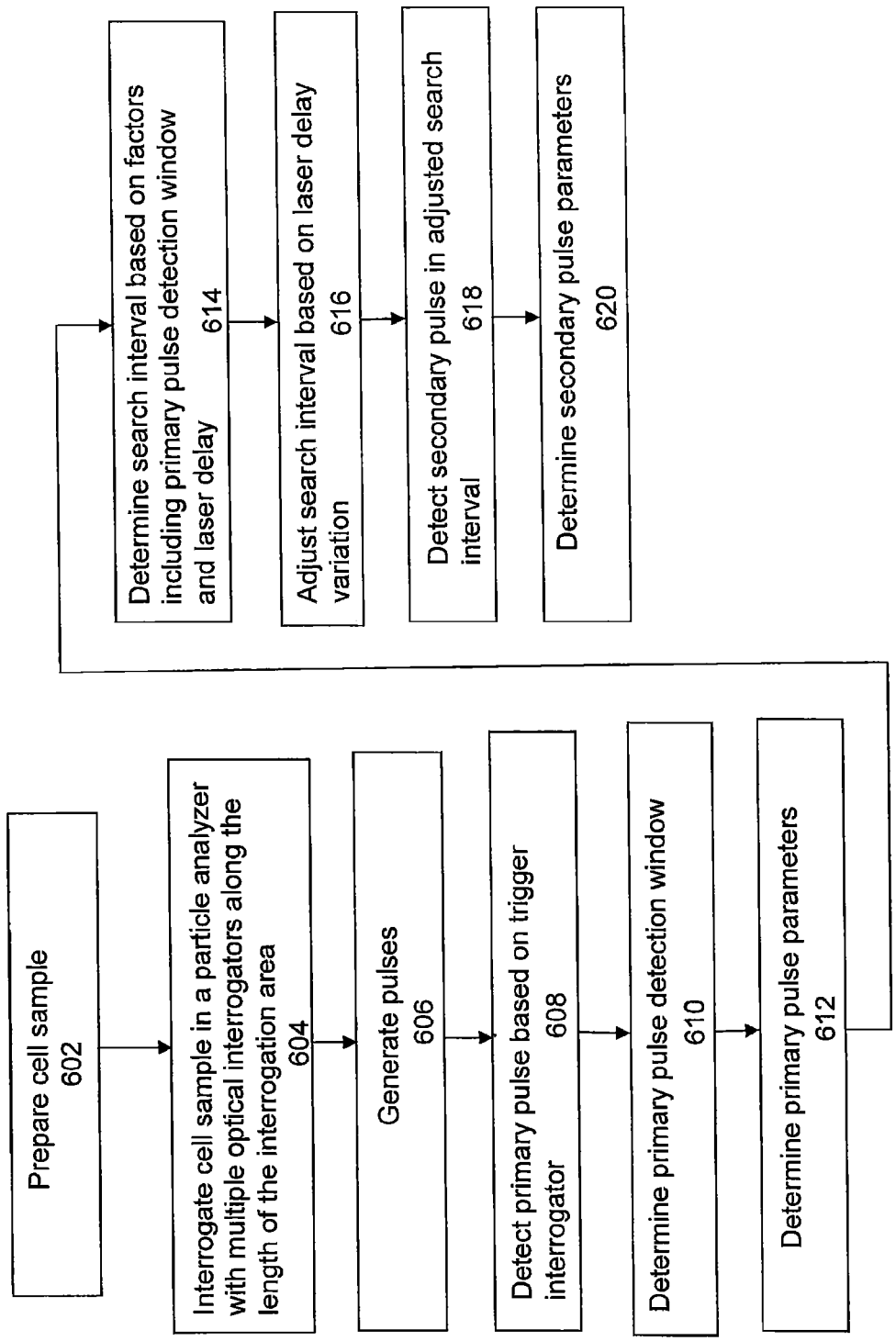
FIG. 6 is an illustration of a method to accurately generate parameters in a particle analyzer, according to an embodiment of the present invention.

FIG. 6 is a flow chart of a method 600 for generating measurement parameters, such as pulse peak, pulse width, and pulse area, for a particle sample in a particle analyzer, according to an embodiment of the present invention.

In step 602, a cellular sample is prepared for analysis in a particle analyzer, such as a flow cytometer. Sample preparation can include marking cells (also referred to as staining) with fluorescents. As mentioned above, fluorescents bind to specific cell types, and can be used to identify those cell types when the cell sample is illuminated with appropriate laser light.

In step 604, the cellular sample is interrogated in the interrogation area. The interrogation of a particle sample includes injection of the sample, with or without perturbation, into the interrogation area and the interrogation of particles by probes along the interrogation area.

The prepared cell sample, together with a sheath fluid, is input to the particle analyzer. The input to the interrogation area can be controlled by configuring various features such as nozzle size and sheath pressure. Nozzle sizes are configured, for example, to accommodate various particle types. The sheath pressure can determine the rate at which the particle stream is injected into the interrogation area. Thus the sheath pressure can be configured according to a desired average velocity of particles within the interrogation area.

In some embodiments, a perturbation signal can be applied to the particle stream. For example, a perturbation generator can introduce a pressure in the form of a sine wave to the particle stream as it exits the nozzle. The perturbation can increase (relative to having no perturbation) velocity differences among the particles as they flow through the interrogation area.

Along the length of the interrogation area, i.e., along the flow path of the cell sample within the interrogation area, multiple optical interrogators are positioned. In an embodiment, the optical interrogators are 7 laser light sources, such as laser diodes, and corresponding optical detectors. The lasers can have wavelength ranges that may or may not overlap. The optical detectors are capable of sensing light scatter, fluorescence, and other optical characteristics. As each particle passes through an interrogation area illuminated by a laser source, the corresponding detector collects the resulting optical signals. In this manner, optical signals corresponding to each active optical interrogator are collected for each particle.

In step 606, pulses corresponding to the interrogations are generated. The optical signals collected by each optical detector are then converted to respective electrical pulses. In an embodiment, the photoelectrical conversion of optical signals to electrical signal can be accomplished by a device such as a photodiode, photomultiplier tube, or the like. In an embodiment, steps 604 and 606 can be performed by particle interrogator 105.

In step 608, the primary pulse is detected. The primary pulse is the pulse relative to which the other pulses of the same particle are measured. The primary pulse is associated with a trigger interrogator, i.e., the interrogator relative to which all other interrogations are measured. In an embodiment, the trigger optical interrogator is the first interrogator in the path of the particle flow. In other embodiments, the trigger interrogator can be selected as any one of the other interrogators. As noted above, users can select different optical interrogators as trigger interrogator based on the type of sample and type of analysis.

In step 610, a primary pulse detection window is determined. The primary pulse detection window is defined by the primary pulse. The two edges of the primary pulse detection window are located at the points where the primary pulse exceeds the predetermined pulse detection threshold value, i.e., on the ascending and descending edges, respectively. Thus, the width of the primary pulse detection window, in an embodiment, is equal to the width of the primary pulse measured between the points at which the pulse exceeds the pulse detection threshold.

In step 612, optionally, parameters corresponding to the primary pulse are calculated. In an embodiment, the parameters calculated include the peak, width, and area of the primary pulse. In an embodiment, the highest value of the pulse within the primary pulse detection window is determined as the pulse peak. For example, a track and hold circuit can be used to determine the peak. In another embodiment, a memory buffer, such as a first in first out (FIFO) buffer can be initialized to null at the beginning of the primary pulse detection window, and updated with each successive value that is higher than the current value in the buffer, as the pulse is traversed throughout the primary pulse detection window.

The primary pulse width, in an embodiment, is determined as the distance (duration) between the half-peak point on the ascending edge of the primary pulse and the half-peak point on the descending edge. Other embodiments can use the distance between the leading and trailing edges of the pulse (the points of intersection with the predetermined pulse detection threshold), or the distance between some percentage-of-peak points on the ascending and descending edges of the pulse.

The primary pulse area is determined by integrating the pulse above a predetermined percentage of peak value. Thus the pulse area is defined by the area under the curve between the points corresponding to a predetermined percentage of peak value. In another embodiment, the pulse area can be determined by integrating the pulse between the points of intersection with the predetermined pulse detection threshold value.

With respect to the particle that triggered the primary pulse, steps 614-620 can be repeated for each interrogator for which a pulse is generated. In step 614, a search interval is determined in which to detect a secondary pulse corresponding to one of the secondary interrogators. The search interval defines a time duration in which the secondary pulse is expected to be detectable in the incoming stream of pulses. In an embodiment, the search interval can be determined based on the primary pulse detection window and the laser delay from the trigger interrogator to a selected secondary interrogator. For example, the search interval can be centered at a distance from the primary pulse detection window that corresponds to the laser delay between the respective trigger and secondary interrogators. The laser delay can be predetermined for each trigger interrogator and secondary interrogator pair. In another embodiment, the laser delay can be determined based on the spatial distance between the trigger interrogator and secondary interrogator, and the average velocity of particles in the interrogation area. The velocity of the particles can be determined from known specifications of the injection nozzle, sheath pressure, or can be estimated based on the width of the primary pulse detection window. In yet other embodiments, the velocity of particles can be determined based on dynamic measurements, such as, for example, measuring the time elapsed for a particle to be detected by interrogators between which the distance is known. Also, as described above with respect to FIG. 4, the amplitude of the applied perturbation, if any, can affect the velocity of the particle and can affect the delay associated with the particle arriving at the corresponding secondary interrogator.

The duration of the search interval can be configured to be equal to the width of the primary pulse detection window. In another embodiment, the duration of the search interval is configured to be equal to the primary pulse detection window plus a predetermined extension. The predetermined window extension can be added equally to both sides of the search interval such that the distance between the centers of the search window and the primary pulse detection window is maintained. In another embodiment, the search interval duration can be set according to a predetermined setting. The extension is introduced to accommodate, to some extent, the variance in arrivals of the pulses with respect to the original detection window. The size of the extension can be statically set, can be set based on the size of the corresponding primary pulse detection window, or can be determined according to the strength of the perturbation. For example, larger extensions can be configured for larger amplitudes of perturbation, and smaller extensions can be configured for small amplitudes.

In an embodiment, a secondary pulse detection window is determined such that it corresponds to the search interval. The secondary pulse detection window, with respect to a selected interrogator, is the time interval during which the incoming stream of pulses are initially examined for the existence of the corresponding secondary pulse. The detection of coincidence and spillover, for example, are based on primary and/or secondary pulse detection windows. The sizing (i.e., setting the duration) of the pulse detection window must balance the tradeoff between making the window too big and permitting increased coincidence events, and making the window small and allowing the pulses to fall outside of the window. Making the pulse detection widows large can also lead to problems of one pulse detection window overlapping the pulse detection window of an adjacent interrogator.

Figure 7:
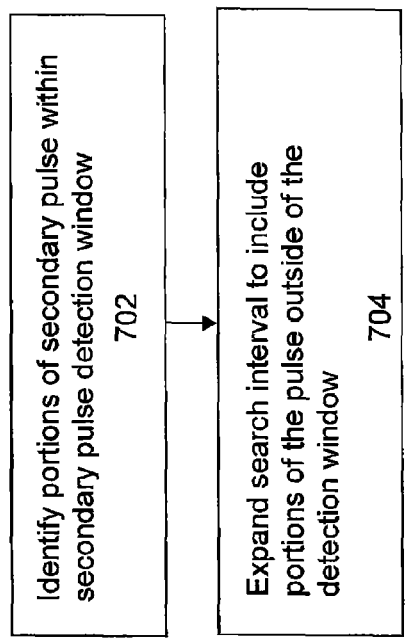
FIG. 7 is an illustration of a method to expand a search interval beyond the secondary pulse detection window, according to an embodiment of the present invention.

In step 616, the search interval is adjusted based upon laser delay variation. In an embodiment, the search interval initially corresponds to the secondary pulse detection window. According to the embodiment, the search interval is expanded to include durations before and/or after the secondary pulse detection window, so that the corresponding pulse can be detected even if it has arrived early or late with respect to the secondary pulse detection window due to laser delay variation. FIG. 7 is an illustration of an embodiment in which the search interval is adjusted by expanding beyond the secondary pulse detection window. In another embodiment, the secondary pulse detection window includes the expanded durations. The expanded durations can be determined, for example, based on the state or amplitude of the perturbation at the time the particle exits the nozzle.

According to some embodiments, for example, embodiments in which the search interval comprising the secondary pulse detection window and the expanded durations, and embodiments in which the search interval corresponds to an expanded secondary pulse detection window, the search interval can be dynamically modified to avoid collisions between adjacent windows. For example, upon detecting a collision of an expanded search interval, the search interval can be truncated, or adjusted, to not overlap the colliding search interval.

Figure 11:
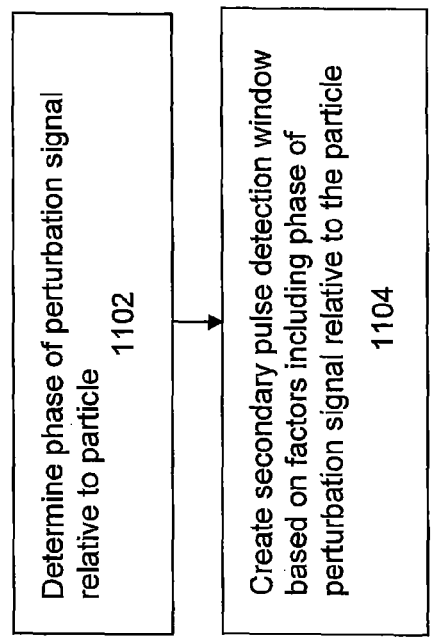
FIG. 11 is an illustration of a method for adjusting the secondary pulse detection window, according to an embodiment of the present invention.

In another embodiment, the search interval corresponds to the secondary pulse detection window, and the search interval is adjusted by shifting or moving it to occur either forward or backward in time with respect to its initial position. The search interval is moved based upon whether the expected laser delay variation will result in the pulse arriving before or after the initial position. FIG. 11 is an illustration of an embodiment in which the search interval and/or a corresponding secondary pulse detection window is moved with respect to its initial position based on expected laser delay variation.

In step 618, the corresponding secondary pulse is detected in relation to the adjusted search interval. In an embodiment, the pulse corresponding to the secondary pulse detection window is determined as the pulse having a substantial portion of it within the corresponding pulse detection window. In an embodiment, if more than one pulse is seen to be within a window, at least partially, the pulse with more of it within the window is considered the pulse corresponding to the respective window. In another embodiment, the pulse with the higher peak value is considered. In other embodiments, the respective window can be adjusted to include only a single pulse.

In step 620, parameters corresponding to the secondary pulse are determined. In an embodiment, having found the corresponding secondary pulse in step 618, the pulse as defined by the pulse above a threshold pulse detection value and/or above a predetermined percentage of peak value is considered regardless of whether the entirety of such portions lie within the secondary interrogation window. For example, in an embodiment, portions of the pulse detected within an expanded search interval are considered along with the portions within the corresponding secondary pulse detection window. In another embodiment, for example, in which the pulse detection window was moved in response to expected laser delay variation, the secondary pulse can be detected based on portions of the pulse substantially within the secondary pulse detection window.

The secondary pulse is processed to determine the pulse peak value based on the entire pulse above the pulse detection threshold. In an embodiment, a track-and-hold circuit can be employed to determine the peak of the pulse. For example, the pulse can be tracked for higher values starting from any previously determined values for the peak of the same pulse, such as a peak value determined at the time the corresponding secondary pulse detection window was created. In another embodiment, a memory buffer, such as a FIFO buffer, can be initialized to null at the point the secondary pulse exceeds the pulse detection threshold and updated with each successive value that is higher than the current value in the buffer, as the pulse is traversed. In yet another embodiment, a FIFO buffer can be initialized with the value of any previous peak determination for the same pulse, such as a peak value determined at the time of secondary pulse detection window creation, and updated with each successive value that is higher than the current value in the buffer as the pulse is traversed.

The secondary pulse can also be processed to determine the pulse width. The secondary pulse width, in an embodiment, is determined as the distance (duration) between the half-peak value on the ascending edge of the primary pulse and the half-peak value point on the descending edge. Other embodiments can use the distance between the leading and trailing edges of the pulse (e.g., the points of intersection with the predetermined pulse detection threshold), or the distance between some percentage-of-peak points on the ascending and descending edges of the pulse.

The secondary pulse area is determined by integrating the pulse above a predetermined percentage of peak value. Thus the pulse area is defined by the area under the curve between the points corresponding to a predetermined percentage of peak value. In another embodiment, the pulse area can be determined by integrating the pulse between the points of intersection with the predetermined pulse detection threshold value.

Calculating pulse parameters for secondary pulses by moving outside of the respective pulse detection windows yield substantial improvements in the accuracy of those parameters. For example, conventionally the peak of a secondary pulse was determined as the highest value within the respective pulse detection window and therefore can not return the actual peak of the pulse in cases where the actual peak was outside the window (e.g. outside the window including the window extensions). In embodiments of the present invention, by moving beyond the detection window to track the secondary pulse, the parameters can be determined with accuracy even when a substantial portion of the pulse lies outside the detection window.

Detecting Pulse Outside of the Pulse Detection Window

FIG. 7 is an illustration of a method 700 to create a search interval that expands beyond a corresponding pulse detection window. In an embodiment, method 700 performs the processing steps of the adjusting step 616 described above.

In step 702, portions of the secondary pulse within the corresponding secondary pulse detection window are detected. The secondary pulse detection window, for example, can be created in step 614 as described above. In an embodiment, the secondary pulse detection window is defined corresponding to the initial search interval for the particle being interrogated.

As noted above, due to laser delay variations, the pulse corresponding to the particle under interrogation can have portions of it arriving before or after the secondary pulse detection window. In step 702, the portions of the pulse that is within the secondary pulse detection window is determined.

In step 704, the search interval is increased to include areas before and/or after the corresponding secondary pulse detection window. For example, if the portions of the pulse within the secondary pulse detection window indicate that the pulse arrived early with respect to the center of the window, then the search window is adjusted by expanding to include a time interval before the secondary pulse detection window. If the portions of the pulse within the secondary pulse detection window indicate that the pulse arrived late with respect to the center of the window, then the search window is adjusted by expanding to include a time interval after the secondary pulse detection window. In another embodiment, if it is determined that the pulse exceeded the secondary pulse detection window both before and after, then the search window is adjusted by expanding to include time intervals both before and after the secondary pulse detection window. The adjusted search window is then used to determine parameters of the secondary pulse, for example, as in steps 618-620 described above.

Determining Peak of Secondary Pulse

Figure 8:
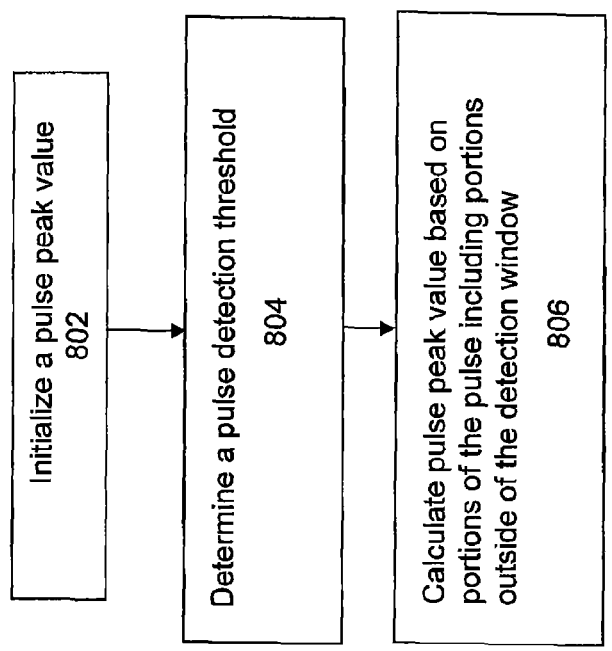
FIG. 8 is an illustration of a method for calculating a peak value of a pulse, according to an embodiment of the present invention.
Figure 10A:
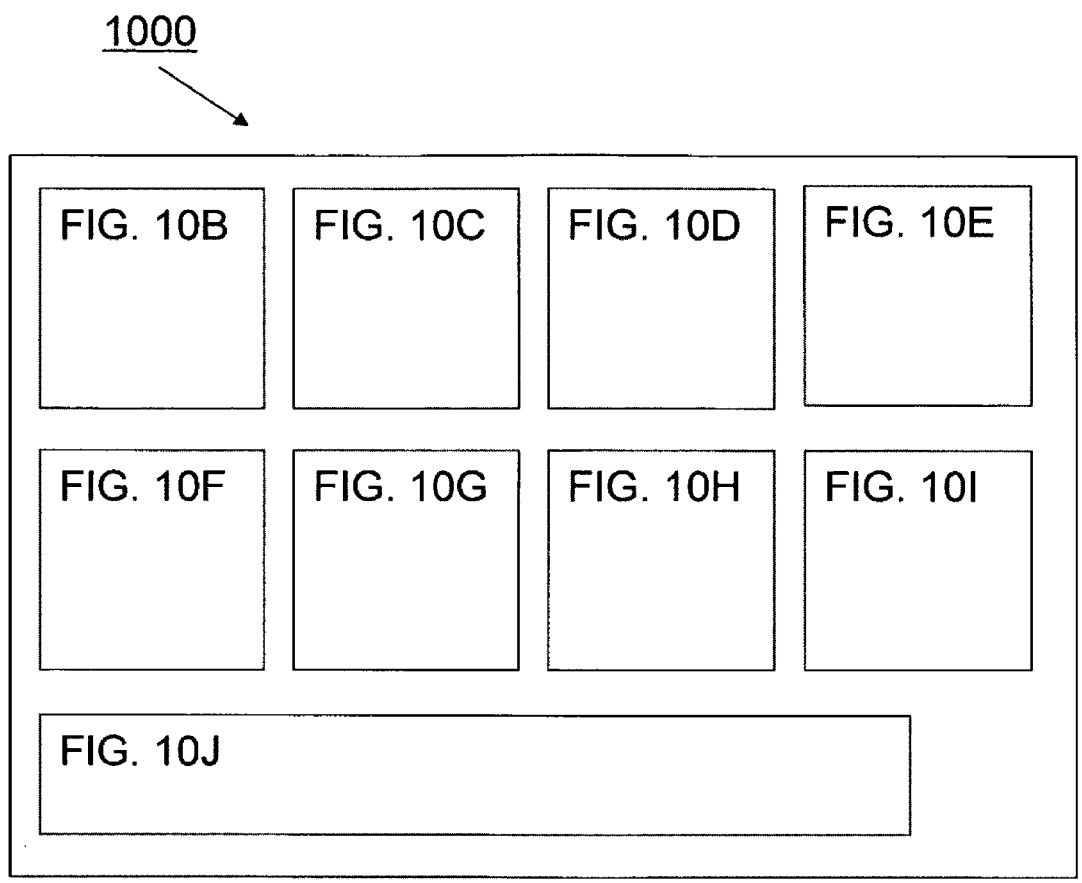
FIG. 10 is an illustration of the relationship between the phase of the perturbation signal applied to the stream, and the arrival time of a pulse relative to the corresponding pulse detection window.
Figure 10B:
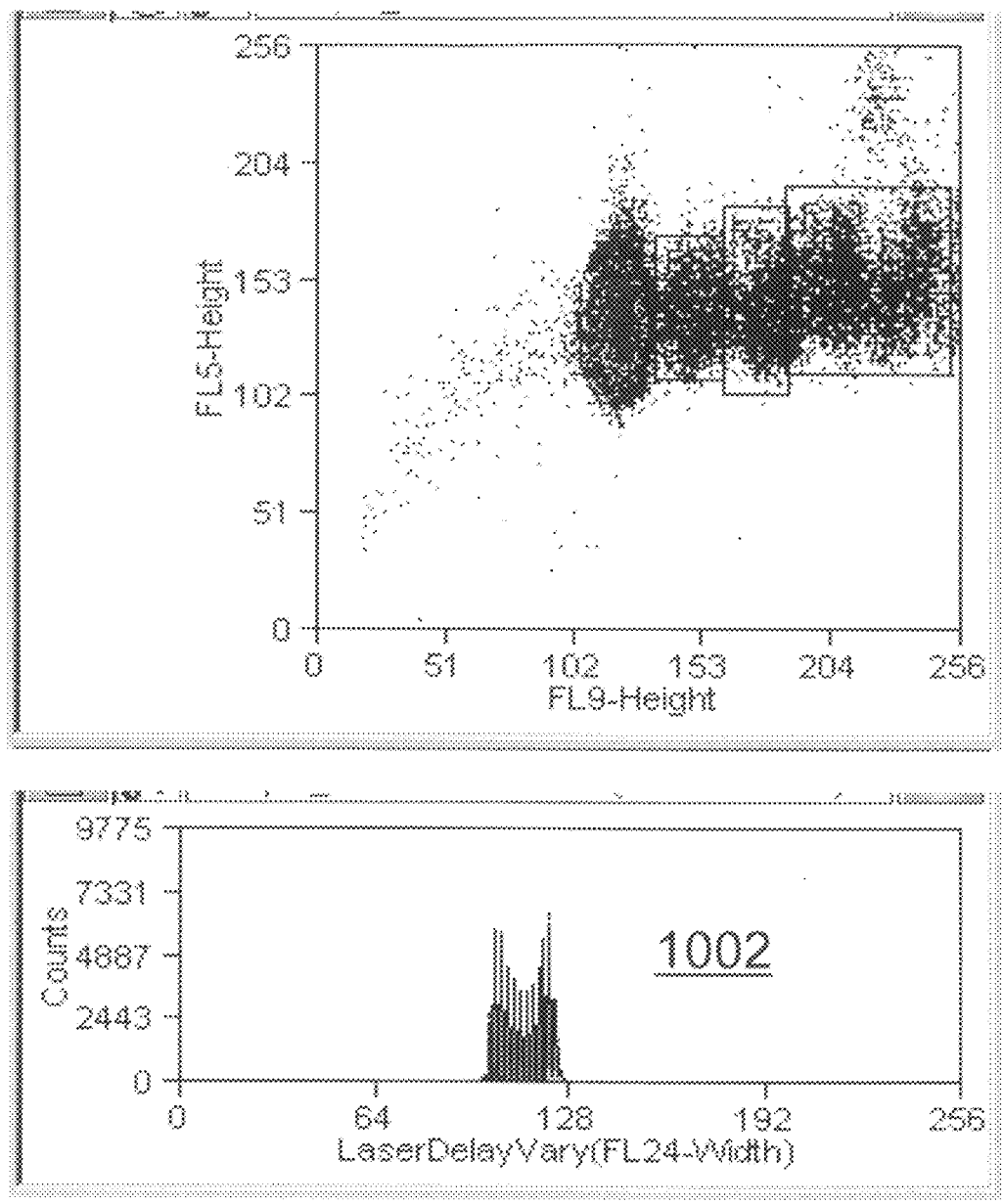
Figure 10C:
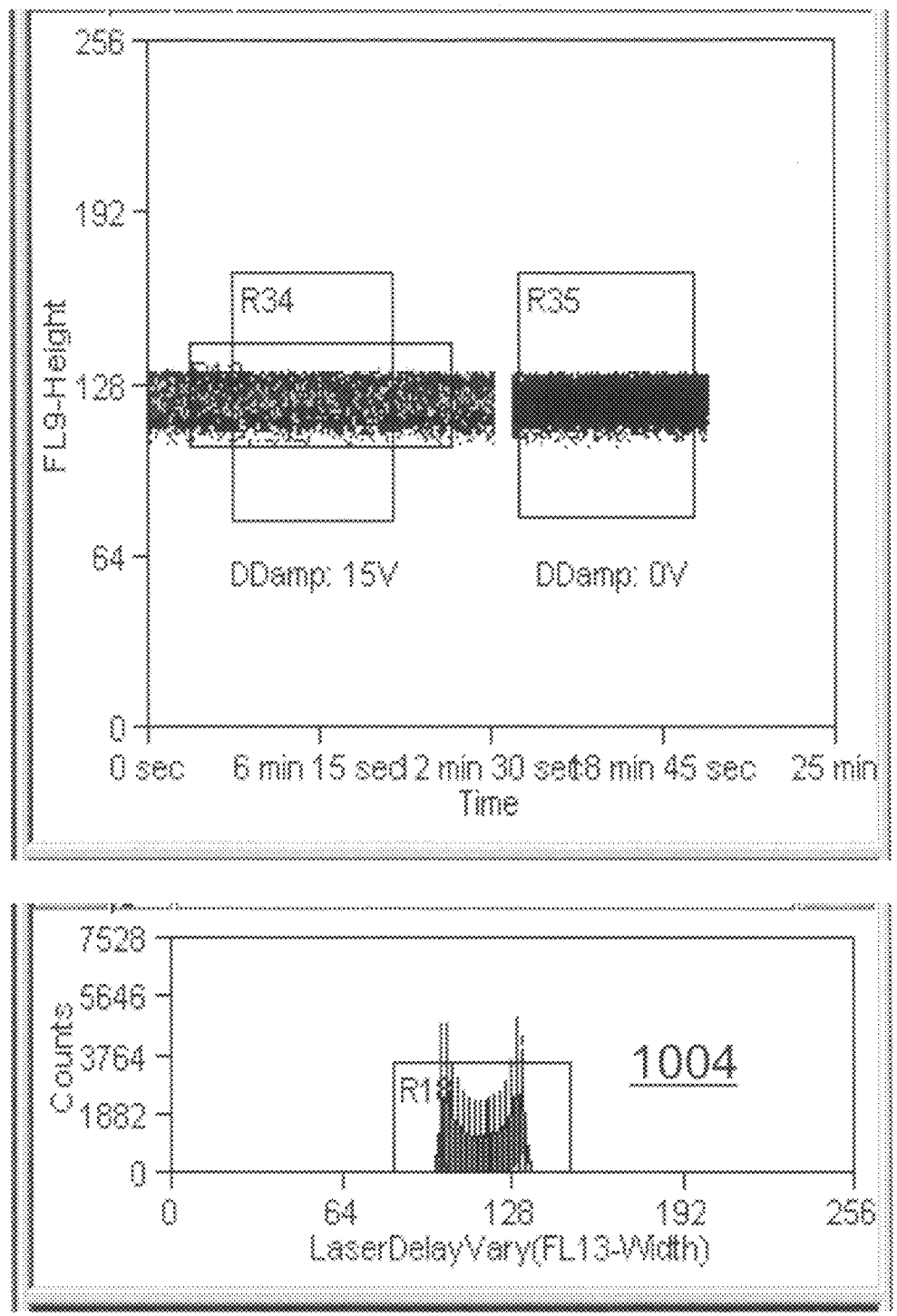
Figure 10D:
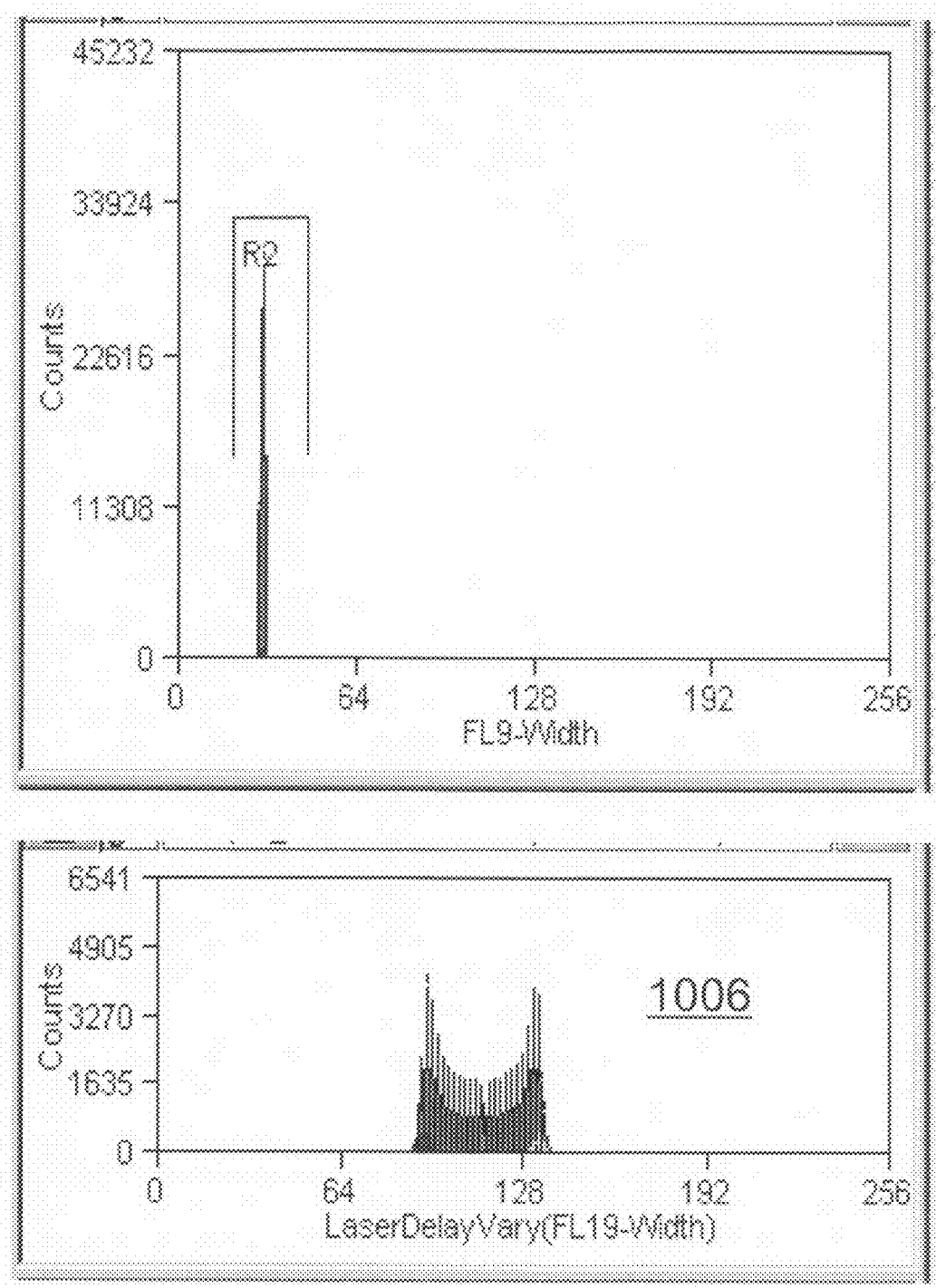
Figure 10E:
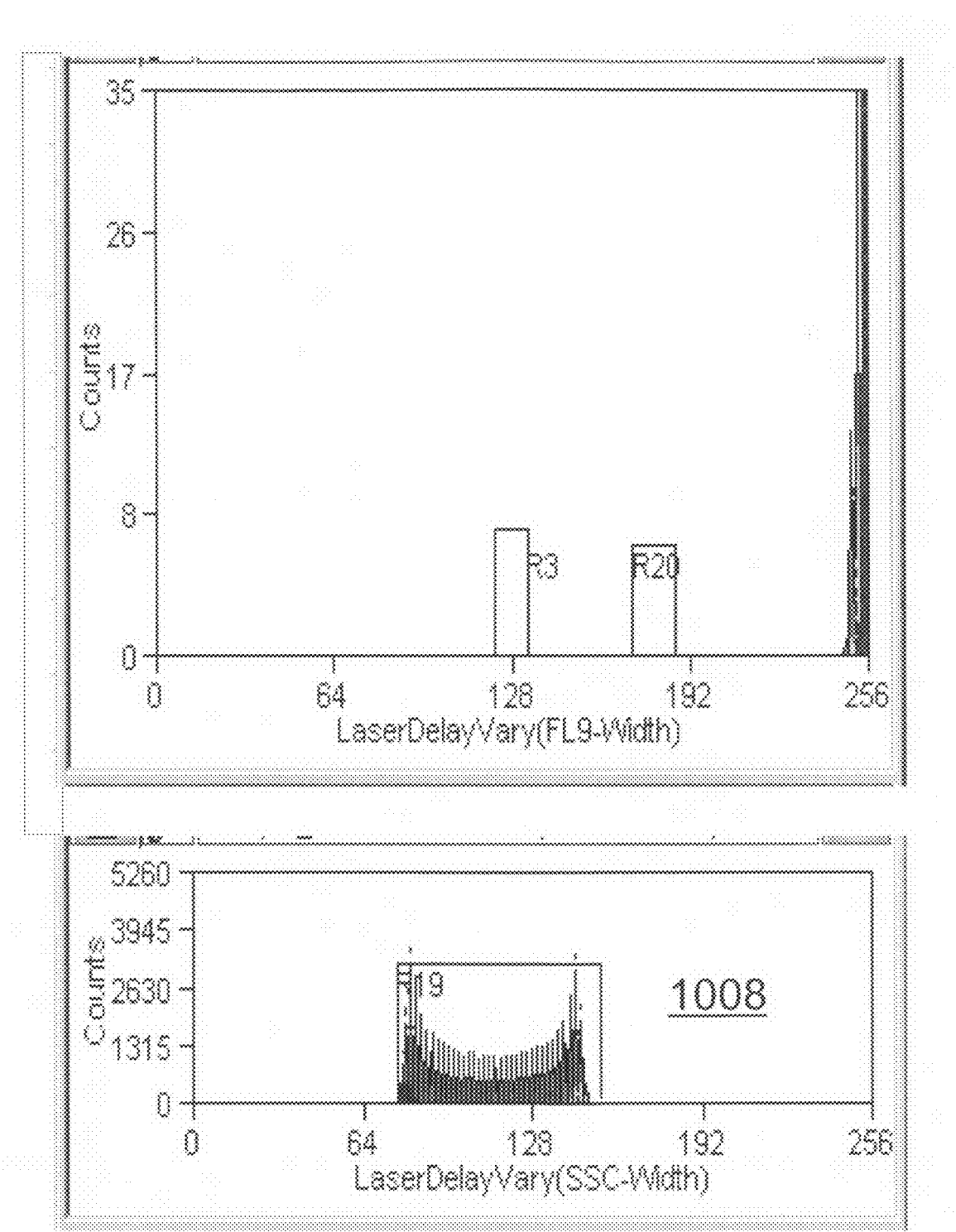
Figure 10F:
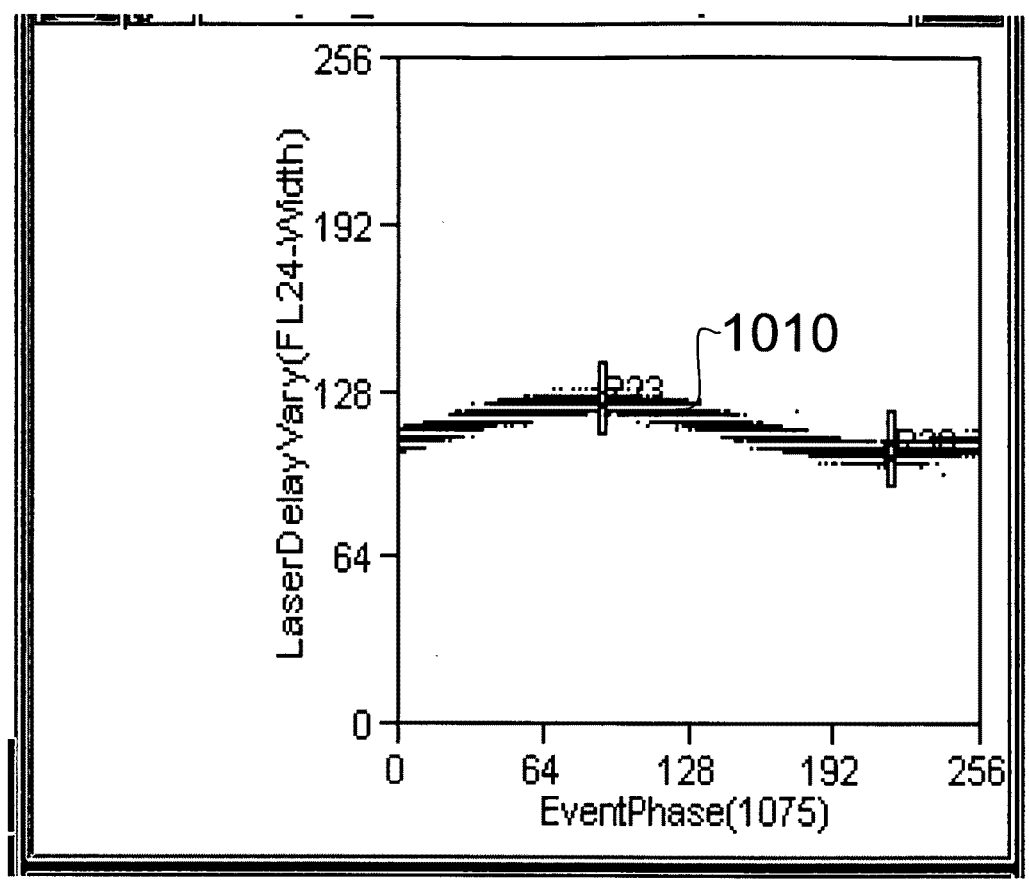
Figure 10G:
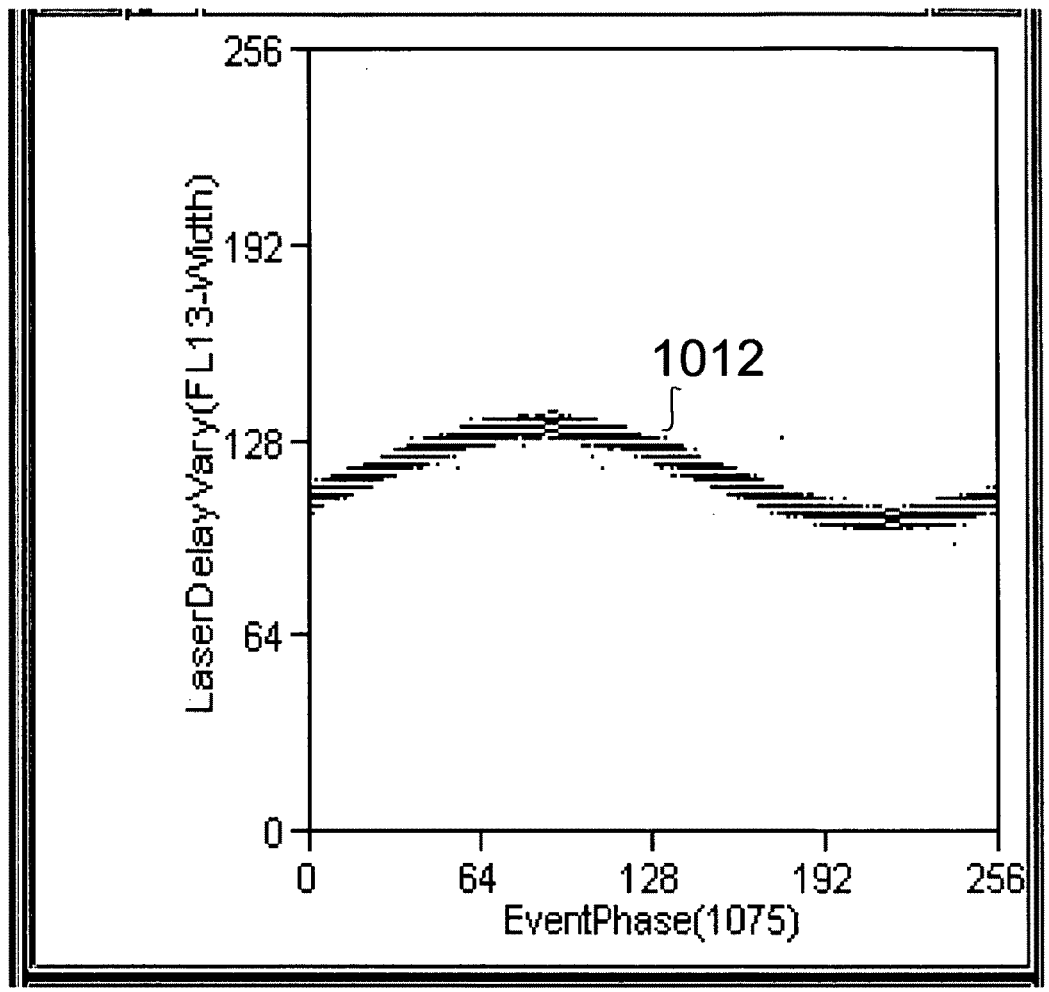
Figure 10H:
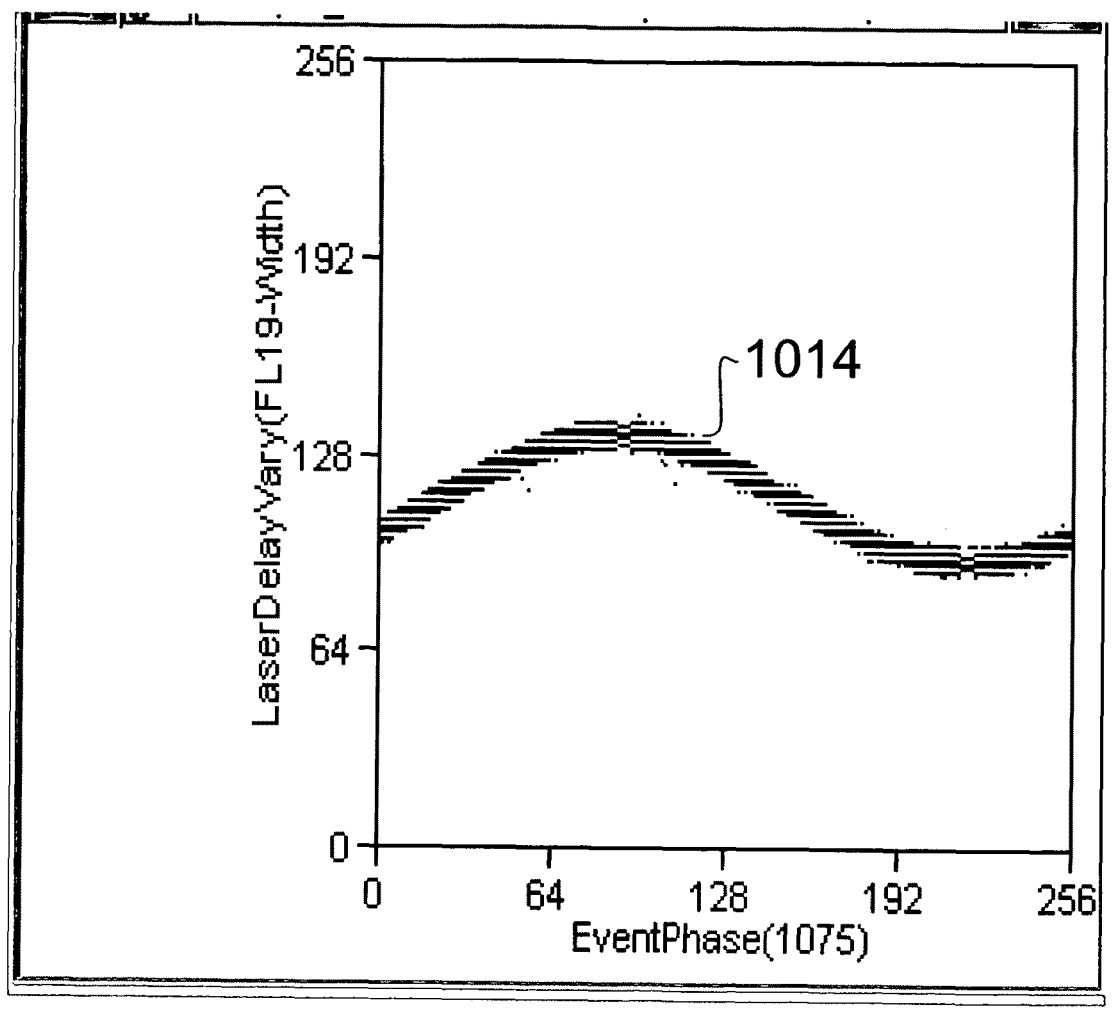
Figure 10I:
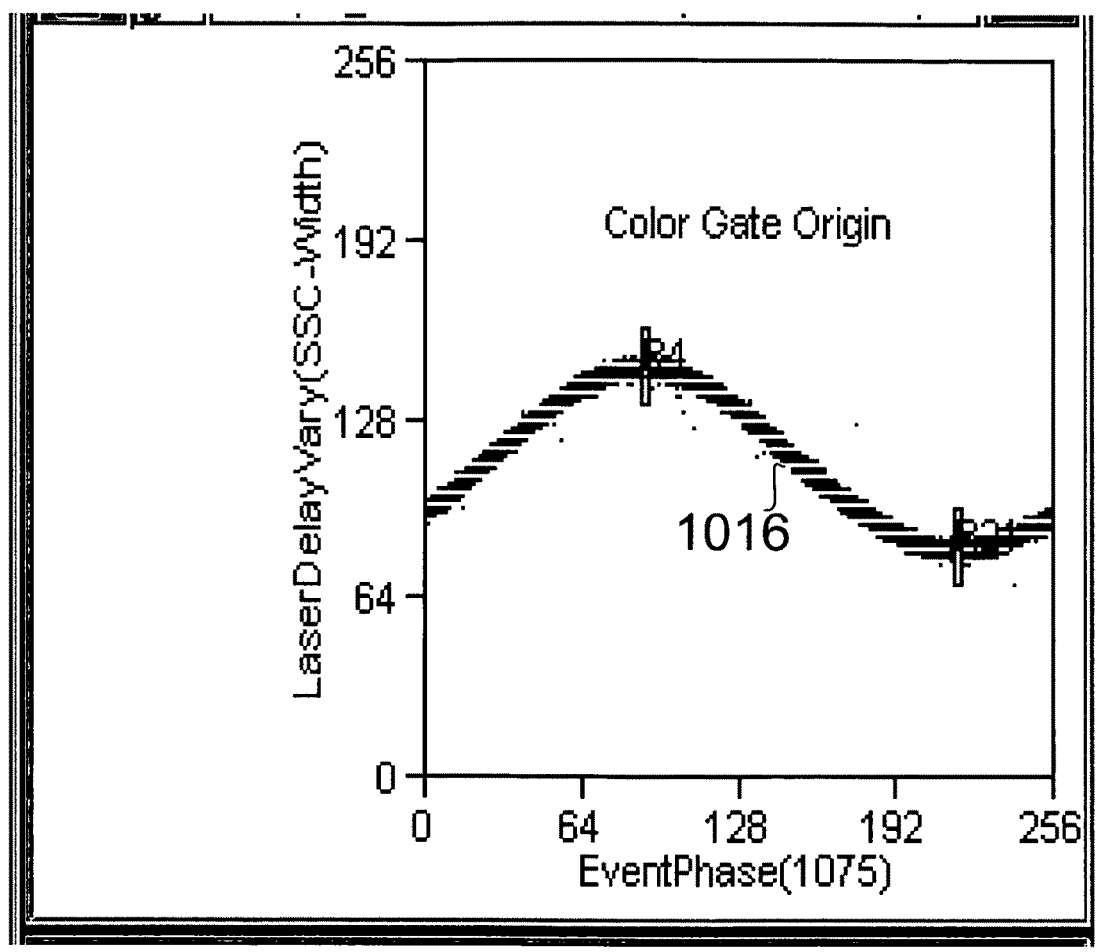
Figure 10J:
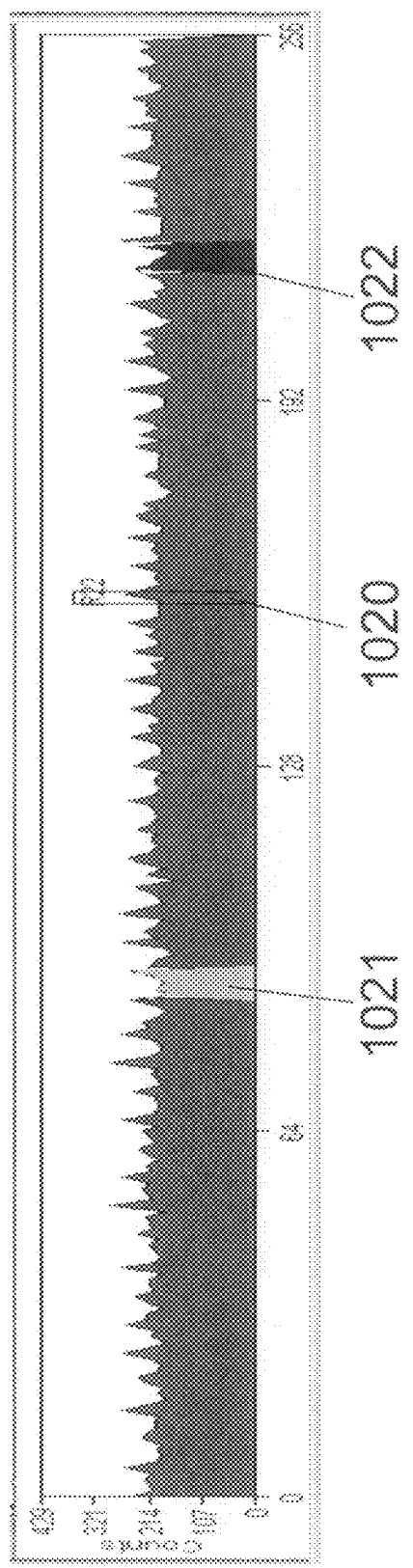

FIG. 8 is a method 800 to determine the peak value of a secondary pulse, according to an embodiment of the present invention. In an embodiment, method 800 can be performed in step 620.

In step 802, the pulse peak value is initialized to the highest value of the corresponding pulse within the detection window.

In step 804, a threshold value for pulse detection is determined. In an embodiment, the threshold is determined as a predetermined percentage of the current peak value. In another embodiment, the threshold is determined as a predetermined percentage of the peak value of the primary pulse. In yet other embodiments, the threshold can be an absolute value or a nominal value above a noise threshold.

In step 806, the pulse, including portions of the pulse outside of the detection window, is processed to determine the actual peak value. For example, in an embodiment, the pulse outside the pulse detection window but within the search interval is processed beginning at the point where it exceeds the detection threshold. In an embodiment, during the processing of the pulse, the highest value of the pulse detected up to that point is repetitively stored in a memory buffer. The value remaining in the buffer at the completion of processing the pulse is taken as the peak value of the secondary pulse.

In an embodiment, step 802 is implemented in a first iteration of processing the pulses, and steps 804 and 806 are implemented in a second iteration of processing. For example, in the first iteration of processing the incoming pulse signals from the particle interrogator, the pulse analyzer can create the windows for the primary and secondary interrogators. The parameters for the primary interrogator can also be determined during the first iteration of processing. Also, for each secondary pulse, an initial peak value can be determined (e.g., such as in step 802 above) during the first iteration of processing. In the second iteration of processing, sometimes also referred to as reprocessing of the pulse signals, the determination of the secondary pulses relative to the previously determined secondary windows and the processing of the secondary pulses by moving beyond the boundaries of the windows can be implemented.

In an embodiment, reprocessing of pulses is implemented by storing the pulses or parts thereof in a FIFO in the order they are received in the pulse analyzer and digitized. The buffers in the FIFO can be processed in a first iteration of processing. Based on the position of the buffers corresponding to the relevant detection windows, and if the relevant buffers are still available in the FIFO, buffers before and after the buffers corresponding to the detection window can be processed in the second iteration of processing.

Setting Secondary Pulse Detection Window

FIG. 9 illustrates a method 900 for creating a search interval and/or secondary pulse detection window, according to an embodiment of the present invention. In an embodiment, method 900 can be included in the processing of step 614 described above to create a search interval and/or secondary pulse detection window.

In step 902, the time at which the primary pulse detection window occurred is determined. In an embodiment, the time is determined as the time at which the window is initiated. In another embodiment, the time is determined as the time at the mid-point of the window.

In step 904, the duration of the primary pulse detection window is determined. The duration (also referred to as the width of the window) of the primary pulse detection window is determined by the duration in which the primary pulse remains above the pulse detection threshold value.

In step 906, the distance between the primary interrogator and the subject secondary interrogator is determined. In an embodiment, this distance can be determined based on configuration information.

In step 908, the velocity of the particle is determined. In an embodiment, the average velocity of particles is determined based on sheath pressure configurations or nozzle configurations. In an embodiment, the velocity of the particle can be determined based on the width of the primary pulse. In another embodiment, the velocity of the particles can be determined based on the configuration of a nozzle through which the cellular sample is injected into the interrogation area. For example, the nozzle can be configured to inject the cellular stream at a predetermined rate of flow.

In step 910, a time of occurrence for the secondary window is determined. In an embodiment, the time of occurrence for the secondary window is calculated based on the time of occurrence for the primary pulse detection window, the distance from the primary interrogator to the secondary interrogator, and the velocity of the particle. In an embodiment, the time of occurrence is determined as the time at which the leading edge of the window occurs. In another embodiment, the time of occurrence is the time at which the mid-point of the window. The time of occurrence is measured to be consistent with the manner in which the time of occurrence of the primary pulse is determined. Measuring distance between the primary and secondary pulse detection windows based upon the center of the respective windows would eliminate the variance introduced by changes to the pulse detection threshold. For example, changing the pulse detection threshold changes the time of occurrence of the primary pulse detection window if the distance is measured from the leading edge of the window because the location of the leading edge of the window changes based on the point at which the pulse reaches the threshold value.

In step 912, the width of the secondary pulse detection window is configured. In an embodiment, the width of the secondary pulse detection window is determined as the width of the primary pulse detection window plus a window extension. The duration of the window extension can be preconfigured or dynamically determined based upon factors such as the corresponding laser delay and perturbation amplitude applied to the cell stream. As described above, when dynamically determining the width of the secondary pulse detection window, the widths of the respective windows can be adjusted to avoid collisions or overlaps with adjacent windows.

Predictive Window Adjustments

FIG. 10 is an illustration 1000 of how the phase of a perturbation signal, such as the perturbation signal applied to the particle stream by perturbation generator 124, introduced to the cell stream impacts the arrival of particles at respective interrogators. In the examples shown, the trigger interrogator was configured to be the first interrogator (i.e., interrogator closest to the nozzle). Graphs 1002, 1004, 1006, and 1008, respectively, show the change in laser delay variance for interrogators 2, 4, 5, and 7 which are located at increasing distances to the trigger interrogator. Likewise, graphs 1010, 1012, 1014, and 1016, show the correspondence of the laser delay variation seen at interrogators 2, 4, 5, and 7, respectively, as a function of the phase of the perturbation signal applied to the cell stream. The graphs illustrate that the variance of the laser delay, i.e., the variance in arrival times, increases as the distance from the primary interrogator is increased. The graphs also illustrate that the laser delays, e.g., arrival times of the particles at the secondary windows, are related to the phase of the perturbation signal. For example, graphs 1010-1016 illustrate waveforms representing the laser delay at each secondary window as a function of the event phase of the perturbation signal. The perturbation signal can be waveform in the shape of a sine wave. For example, the variation in the amplitude of the perturbation wave can be a sine wave. Graphs 1010-1016 show sine waves that correspond to the sine wave generated at the perturbation generator that introduces the perturbation signal to the cell stream. Graph 1018 illustrates the particles 1021 that arrived before and the particles 1022 that arrived after the mid-point of the statically set window 1020. Populations 1021 and 1022 correspond to the aggregation of color-gated values at the top and bottom, respectively, of the sine waves shown in graphs 1010-1016. Thus, it is observed that the arrival relative to a statically set window at a secondary interrogator can be viewed as a function of the perturbation signal, or more specifically, the phase of the perturbation signal.

FIG. 11 is method 1100 to predictively determine a secondary pulse detection window, according to an embodiment of the present invention. In an embodiment, method 1100 can be performed in adjusting step 616, described above, to adjust a search interval and/or corresponding secondary pulse detection window.

In step 1102, the phase of the perturbation signal is determined relative to a particle. For example, the phase of the perturbation signal, e.g. whether it is in the positive phase or the negative phase of a sine wave is determined. This can be determined by tracking the phase of the perturbation wave and relating it to the particle at the first interrogator. In an embodiment, a particle seen at the first interrogator is related to the phase of the perturbation signal subject to a predetermined delay.

In step 1104, the secondary pulse detection window is determined, according to an embodiment of the present invention. In an embodiment, a statically set or dynamically determined secondary pulse detection window is moved based on the phase of the perturbation signal relative to the particle. For example, if the particle is related to the positive part of the sine wave representing the perturbation signal, then the detection window can be advanced from its current position, and if the particle is related to the negative part of the sine wave representing the perturbation signal, then the detection window can be delayed with respect to its current position. Furthermore, in an embodiment, the window width of the detection window can be adjusted based on the amplitude of the sine wave at the position related to the particle. For example, the window can be made wider for larger amplitudes, and narrower for smaller amplitudes.

The foregoing description of the invention has been presented for purposes of illustration and description. It is not intended to be exhaustive or to limit the invention to the precise form disclosed, and other modifications and variations may be possible in light of the above teachings. The embodiment was chosen and described in order to best explain the principles of the invention and its practical application to thereby enable others skilled in the art to best utilize the invention in various embodiments and various modifications as are suited to the particular use contemplated. It is intended that the appended claims be construed to include other alternative embodiments of the invention except insofar as limited by the prior art.

The invention claimed is:

1. A method of generating measurement parameters for a particle sample in a particle analyzer, comprising:
   (a) interrogating the particle sample with interrogators respectively positioned along a length of an interrogation area, the interrogators comprising a triggering interrogator and one or more secondary interrogators;
   (b) generating respective pulses based upon the interrogation of a first particle from the particle sample, wherein the pulses comprise a triggering pulse corresponding to the triggering interrogator and a secondary pulse corresponding to one of the secondary interrogators;
   (c) determining a primary pulse detection window based upon the triggering pulse;
   (d) determining a search interval to find the secondary pulse based upon factors including the primary pulse detection window and a velocity of the first particle;
   (e) adjusting the search interval for variation in the velocity of the first particle dynamically based on the interrogation of the first particle;
   (f) identifying the secondary pulse in the adjusted search interval; and
   (g) processing the secondary pulse to determine a peak value of the secondary pulse.

2. The method of claim 1, further comprising: (h) processing the secondary pulse to determine a pulse width value of the secondary pulse.

3. The method of claim 2, wherein the pulse width value is a predetermined percentage of the peak value of the secondary pulse.

4. The method of claim 1, wherein the adjusting step (e) comprises:
determining a size of adjustment based upon the interrogation of the first particle; and
increasing the search interval in proportion to the size of the adjustment.

5. The method of claim 1, wherein the search interval comprises a secondary pulse detection window determined based upon factors including the primary pulse detection window and the velocity of the first particle, and wherein the adjusting step (e) comprises: identifying portions of the secondary pulse in the secondary pulse detection window; and expanding the search interval to include portions of the secondary pulse outside of the secondary pulse detection window.

6. The method of claim 5, wherein a duration of the secondary pulse detection window substantially equals a duration of the primary pulse detection window plus a predetermined window extension.

7. The method of claim 5, wherein processing the secondary pulse step (g) comprises: (i) determining an initial peak value for the secondary pulse based upon portions of the secondary pulse inside the secondary pulse detection window;
(ii) detecting the secondary pulse at a predetermined threshold of the initial peak value; and
(iii) repetitively storing a highest value detected for the secondary pulse.

8. The method of claim 7, wherein steps (ii)-(iii) are performed during a reprocessing of the secondary pulse.

9. The method of claim 1, wherein determining a search interval step (d) comprises:
determining a time of occurrence for the primary pulse detection window;
determining a laser delay between the triggering interrogator and the secondary interrogator; and
calculating a time of occurrence for the secondary pulse detection window based upon the time of occurrence for the primary pulse detection window and the laser delay.

10. The method of claim 9, wherein the laser delay is determined based on a separation distance from the primary interrogator to the secondary interrogator and a velocity of the first particle.

11. The method of claim 9, wherein the determining a search interval step (d) further comprises:
determining a duration of the primary pulse detection window; and
setting a duration of the secondary pulse detection window based on the duration of the primary pulse detection window.

12. The method of claim 11, wherein the setting the duration of the secondary pulse detection window is further based on a predetermined window extension.

13. The method of claim 10, wherein the distance is measured from the center of the primary pulse detection window.

14. The method of claim 1, wherein step (c) comprises:
detecting a first and second position on the triggering pulse corresponding to a predetermined pulse threshold; and
determining the primary pulse detection window based upon the first and second positions.

15. The method of claim 1, wherein the search interval comprises a secondary pulse detection window determined based upon factors including the primary pulse detection window and the velocity of the first particle, and wherein the adjusting step (e) comprises:
detecting characteristics of a perturbation signal applied to the first particle; and
shifting the secondary pulse detection window based upon factors including the primary pulse detection window and the characteristics of the perturbation signal.

16. The method of claim 15, wherein the perturbation signal is applied at a nozzle through which the particle sample is passed, and wherein the nozzle is positioned before the interrogators.

17. The method of claim 15, wherein the characteristics include a phase of the perturbation signal during which the signal is applied to the first particle.

18. The method of claim 17, wherein the perturbation signal is a sine wave.

19. The method of claim 1, further comprising:
(i) reporting the peak value of the secondary pulse.

20. A method of generating measurement parameters for a particle sample in a particle analyzer, comprising:
(a) interrogating the particle sample with interrogators respectively positioned along a length of an interrogation area, the interrogators comprising a triggering interrogator and one or more secondary interrogators;
(b) generating respective pulses based upon the interrogation of a first particle from the particle sample, wherein the pulses comprise a triggering pulse corresponding to the triggering interrogator and a secondary pulse corresponding to one of the secondary interrogators;
(c) determining a primary pulse detection window based upon the triggering pulse;
(d) determining a secondary pulse detection window based upon factors including the primary pulse detection window and a velocity of the first particle;
(e) detecting characteristics of a perturbation signal applied to the first particle;
(f) shifting the secondary pulse detection window based upon the characteristics of the perturbation signal;
(g) identifying the secondary pulse in an adjusted search interval; and
(h) processing the secondary pulse to determine measurement parameters of the secondary pulse.

21. A particle analyzer, comprising:
at least one processor;
a particle interrogator coupled to the at least one processor and configured to: interrogate a particle sample with interrogators respectively positioned along a length of a particle flow, the interrogators comprising a triggering interrogator and one or more secondary interrogators; and
generate respective pulses based upon the interrogation of a first particle from the particle sample, wherein the pulses comprise a triggering pulse corresponding to the triggering interrogator and a secondary pulse corresponding to one of the secondary interrogators; and
a pulse analyzer coupled to the at least one processor and comprising:
a primary pulse detection window creator configured to:
determine a primary pulse detection window based upon the triggering pulse;
a secondary pulse detection window creator configured to:
determine a search interval to find the secondary pulse based upon factors including the primary pulse detection window and a velocity of the first particle; and
adjust the search interval for variation in the velocity of the first particle dynamically based on the first particle; and a secondary pulse parameter generator configured to:
identify, the secondary pulse in the adjusted search interval; and
process the secondary pulse to determine a peak value of the secondary pulse.

22. The apparatus of claim 21, further comprising:
a data analyzer coupled to the at least one processor and configured to receive parameters from the pulse analyzer; and
a display coupled to the at least one processor.

23. The apparatus of claim 21, wherein the search interval comprises a secondary pulse detection window determined based upon factors including the primary pulse detection window and the velocity of the first particle, and wherein the secondary pulse detection window creator is further configured to:
identify portions of the secondary pulse in the secondary pulse detection window; and
expand the search interval to include portions of the secondary pulse outside of the secondary pulse detection window.

24. The apparatus of claim 21, wherein the search interval comprises a secondary pulse detection window determined based upon factors including the primary pulse detection window and the velocity of the first particle, and wherein the secondary pulse detection window creator is further configured to:
detect characteristics of a perturbation signal applied to the first particle; and
shift the secondary pulse detection window based upon factors including the primary pulse detection window and the characteristics of the perturbation signal.

25. A computer program product comprising a non-transitory computer usable medium having control logic stored therein for causing a computer to generate parameters for a particle sample with interrogators respectively positioned along a length of an interrogation area, the interrogators comprising a triggering interrogator and one or more secondary interrogators, said control logic comprising:
determining a primary pulse detection window based upon a triggering pulse;
determining a search interval to find the secondary pulse based upon factors including the primary pulse detection window and a velocity of the first particle;
adjusting the search interval for variation in the velocity of the first particle dynamically based on the first particle;
identifying the secondary pulse in the adjusted search interval; and
processing the secondary pulse to determine a peak value of the secondary pulse.

* * * * *